United States Patent
Fukui

(10) Patent No.: US 7,079,979 B2
(45) Date of Patent: Jul. 18, 2006

(54) INSPECTION METHOD, INSPECTION APPARATUS, AND FACILITY DIAGNOSIS UNIT

(75) Inventor: Ikuma Fukui, Moriyama (JP)

(73) Assignee: Omron Corporation, Kyoto (JP)

(*) Notice: Subject to any disclaimer, the term of this patent is extended or adjusted under 35 U.S.C. 154(b) by 30 days.

(21) Appl. No.: 10/944,414

(22) Filed: Sep. 20, 2004

(65) Prior Publication Data

US 2005/0114081 A1   May 26, 2005

(30) Foreign Application Priority Data

Sep. 22, 2003   (JP)   ............................. 2003-330567
Sep. 14, 2004   (JP)   ............................. 2004-267529

(51) Int. Cl.
*G06F 11/30*   (2006.01)

(52) U.S. Cl. ..................... 702/182; 382/228; 702/34; 702/83

(58) Field of Classification Search ............ 702/34–35, 702/73, 81–84, 181–185; 700/142; 324/379, 324/394; 714/23, 29; 250/311; 382/228

See application file for complete search history.

(56) References Cited

U.S. PATENT DOCUMENTS 5,210,704 A * 5/1993 Husseiny ..................... 702/34
5,566,092 A * 10/1996 Wang et al. ................ 702/185

FOREIGN PATENT DOCUMENTS

| JP | 11-173909 | 7/1999 |
| JP | 11-173956 | 7/1999 |
| JP | 2001-091414 | 4/2001 |

* cited by examiner

*Primary Examiner*—Michael Nghiem
*Assistant Examiner*—John H. Le
(74) *Attorney, Agent, or Firm*—Foley & Lardner LLP

(57) ABSTRACT

To inspect a status of an inspection object by using an inspection apparatus for extracting amount of characteristic to an inputted waveform signal and determining a status on the basis of the extracted amount of characteristic. Specifically, the inspection apparatus uses a normal knowledge that is generated on the basis of only the data of a normal status at an initial stage to determine whether or not the status of the inspection object complies with the normal status. The inspection apparatus generates an abnormal kind knowledge by abnormal kind on the basis of the data of an abnormal status that are collected in accordance with repeat of the determination, and then, determines the status by using the normal knowledge and the abnormal kind knowledge.

10 Claims, 26 Drawing Sheets

ABNORMALITIES CANNOT BE CLASSIFIED

MASS PRODUCT

WHEN THERE ARE MANY NORMAL PRODUCT DISTRIBUTION DATA THAT ARE PICKED UP, CLOSE TO NORMAL DISTRIBUTION

Fig. 7

| NO | HISTORY | RMS | XP | AMXA | |
|----|---------|-----|----|------|---|
| 01 | NORMAL | 724 | 13 | 0123 | ......... |
| 02 | NORMAL | 755 | 21 | 0234 | ......... |
| 03 | NORMAL | 690 | 12 | 0345 | ......... |
| 04 | NORMAL | 699 | 14 | 0245 | ......... |
| 05 | ABNORMAL A | 723 | 15 | 0135 | ......... |
| 06 | NORMAL | 754 | 12 | 0159 | ......... |
| 07 | ABNORMAL | 734 | 15 | 0203 | ......... |
| 08 | ABNORMAL B | 734 | 14 | 0250 | ......... |

Fig. 8A

| NO | HISTORY | RMS | XP | AMXA | |
|----|---------|-----|----|----|---|
| 01 | NORMAL | 724 | 13 | 0123 | ............ |
| 02 | NORMAL | 755 | 21 | 0234 | ............ |
| 03 | NORMAL | 690 | 12 | 0345 | ............ |
| 04 | NORMAL | 699 | 14 | 0245 | ............ |
| 06 | NORMAL | 754 | 12 | 0159 | ............ |
| . | . | . | . | | ............ |
| . | . | . | . | | ............ |
| . | . | . | . | | ............ |

Fig. 8B

| NO | HISTORY | RMS | XP | AMXA | |
|----|---------|-----|----|----|---|
| 07 | ABNORMAL | 734 | 15 | 0203 | ............ |

| NO | HISTORY | RMS | XP | AMXA | |
|----|---------|-----|----|----|---|
| 05 | ABNORMAL A | 723 | 15 | 0135 | ............ |

| NO | HISTORY | RMS | XP | AMXA | |
|----|---------|-----|----|----|---|
| 08 | ABNORMAL B | 734 | 14 | 0250 | ............ |
| . | | . | . | | ............ |
| . | | . | . | | ............ |
| . | | . | . | | ............ |

INSPECTION METHOD, INSPECTION APPARATUS, AND FACILITY DIAGNOSIS UNIT

BACKGROUND OF THE INVENTION

1. Field of the Invention

The present invention relates to an inspection method, an inspection apparatus, and a facility diagnosis unit.

2. Description of the Related Art

There is an inspection apparatus that takes in a sound or a vibration from an inspection object and inspects if the object is normal or abnormal. The inspection apparatus is used for product inspection and facility diagnosis. According to the facility diagnosis, it is inspected if a working machine and a productive facility operate normally and if it is about time that maintenance such as care and adjustment is necessary on the basis of the vibration and the sound generated by the working machine and the productive facility itself. Specifically, as the facility diagnosis unit, there are an NC finishing machine, a semiconductor plant, and a food plant or the like. According to the product inspection, it is inspected if the product is a normal one or a defective good on the basis of the vibration and the sound generated by the product. It is common to both of them that the inspection is made on the basis of the vibration and the sound. At first, the product inspection will be mainly explained. Some products to be manufactured by the productive facility and a productive system may incorporate a sound source and a vibration source in their insides. In addition, some products may generate a sound or a vibration by their operations. For example, a part such as a motor is incorporated in an electric household appliance such as a refrigerator, an air conditioner, and a washing machine, and if the electric household appliance is driven, it may generate the sound and the vibration in accordance with the rotation of the motor. For example, in an automobile, there are the sound sources or the vibration sources in many parts such as an engine, a power steering, a power sheet, a transmission, and other places.

Some of the sounds and the vibrations of such products may be naturally generated due to the normal operation and other of them may be generated due to the defective operation. The abnormal sound and the abnormal vibration due to the defective operation are caused by abnormal contact in the motor, abnormality of a bearing at a rolling mechanism part, abnormal contact in the rolling mechanism, unbalance of the rolling mechanism, and interfusion of a foreign material or the like. More specifically, there is an abnormal sound such that a rolling part and a fixed part in the motor are rubbed with each other during the rotation only for a moment as an example of the abnormal sound generated by the operation of the mechanism. Some abnormal sounds in the rolling mechanism may be generated due to lack of a gear occurred with frequency once per rotation of a rolling gear, engagement of the foreign material into the gear, and a spot scratch of the bearing or the like. In addition, a sound that a person feels unpleasant may include a sound like "Ki" that is mixed in a prescribed operational sound only for a moment. If only a prescribed operational sound is audible in the normal good, it is possible to regard the product causing the sound like "Ki" as a defective good.

In addition, a pottery product and the product composed of a combination of resin products have no part as the sound source and the vibration sound in itself, however, there is a case that they are inspected if they have a crack or the like. According to the inspection of these products, they are inspected by a sound occurred by hitting the pottery and the resin of the inspection object with a machine tool such as a hammer or the like. If there is no crack in the object, a high tone is generated, and if there is a crack therein, a low tone is generated, so that the inspection can be carried out by this difference in the tone.

In the meantime, "a sound" in the specification may include a sound and a vibration. In the specification, an abnormal sound and an abnormal vibration are generically named as "an abnormal sound" or "an abnormal noise". In addition, in the specification, "a vibration" is used in the meaning of the vibration and the sound.

It is feared that the sound due to the abnormality and the defect not only may make a person to feel unpleasant but also may occur a failure in the product itself. The good products should be separated from the products causing such sounds by inspecting them in a production process. Therefore, in a production plant, "an organoleptic test" depending on five senses such as an acoustic sense and a sense of touch or the like is normally carried out by an examiner so as to determine if there is an abnormal sound. Specifically, the examiner checks the vibration by hearing a sound by his or her ears and touching the product by his or her hands. In the meantime, the organoleptic test is defined by Z8144 of an organoleptic test terminology JIS (Japanese Industrial Standards).

In the meantime, the organoleptic test depending on the five senses of the examiner requires a skilled examiner and further, the determination result may vary widely depending on individual differences. Moreover, this involves a problem such that it is difficult to have data and numeric values of the determination result of the organoleptic test and its management is also difficult. Therefore, in order to solve such a problem, an abnormal noise inspection apparatus aimed at an inspection based on a quantitative and clear standard is presented. This abnormal noise inspection apparatus is designed to automate an "organoleptic test" step and according to this abnormal noise inspection apparatus, the vibration and the sound of a product driving part is measured by a sensor and an analog signal taken into by the sensor is analyzed and inspected (patent documents JP-A-11-173956, JP-A-11-173909, and JP-A-01-91414). As an analytical method of an analog signal waveform taken into by the sensor, there is a method to apply a band pass filter other than an FFT algorithm.

When inspecting the product by device of such an abnormal noise inspection apparatus, it is necessary that the skilled examiner compares the sample data of the waveform data of the normal product with the sample data of the waveform data of the defective product in advance to find a different between them. Then, the examiner sets and inputs an inspection condition (a model rule and a parameter) so that the abnormal noise inspection apparatus may determine and process the difference between the normal product and the defective product.

The technologies disclosed in these patent documents JP-A-11-173956 to JP-A-01-91414 will be briefly explained below. The technologies relate to a frequency analytical apparatus applying an FFT algorithm and it abstracts a time region component of the taken vibration waveform from a frequency region by device of a fast Fourier transformation algorithm. Obtaining an amount of characteristic of the corresponding component on the basis of an abnormal characteristic that is found from among the extracted frequency components, the abnormality is determined on the basis of the amount of characteristic and the determination result of the abnormality is outputted.

It is a matter of course that the extracted amount of characteristic is not limited to the frequency component. There is an effective value of the waveform data on the basis of the vibration and the sound generated from the inspection object, the maximum vibration level, and the number of climaxes and others various kinds of things. In accordance with enlargement of the kinds of the inspection object, the kind of the amount of characteristic is also increased.

A conventional inspection apparatus extracts the amount of characteristic from among the waveform data on the basis of the vibration and the sound that are generated from the inspection object so as to determine whether or not the inspection object complies with a model rule that has been prepared in advance, and the model rule is only based on the defective product such as the frequency component corresponding to the above-described generation region of the abnormal vibration and the abnormal sound. Then, when the object does not correspond to the defective product, the apparatus determines that the product is a normal product.

In other words, in order to design such an inspection apparatus, at first, a plurality of the sample data of the defective products and the sample data of the normal products of the inspection object are prepared, and comparing both, a difference of the characteristic is found. The amount of characteristic that is suitable for only extracting the defective product as compared to a vibration characteristic of the normal product or a sound characteristic thereof is found on the basis of the sample data of the defective product, and a model rule for determining the discrimination between the normal product and the defective product is made and registered. This model rule is a determination algorithm for determining the normal product and the defective product and it is a common rule that can be applied to any of the plural sample data. Conventionally, there are various methods with related to how to find the amount of characteristic suitable for determination, how to extract the amount of characteristic effectively, and how to find a determination algorithm. In any case, it is an essential condition to decide a model rule on the basis of the sample data of the defective product and this is a defined fact and a stereotype.

In the case that the sample data of the defective product cannot be prepared, the model rule cannot be developed, so that this involves a problem such that the inspection apparatus cannot be designed. Further, in order to determine what kinds of abnormality, it is necessary to prepare the sample data for each kind of defect, however, sometimes the sample cannot be obtained well at an initial status upon starting a productive line. In addition, according to such an inspection of the defective product or the apparatus to inspect the kinds of the defect, only the defective product of which sample data is prepared and of which model rule has been made can be determined and it is difficult to detect an unknown defective product.

On the other hand, a determination of good or bad on the basis of the sample data of the defective product as a conventional case is suitable for a productive facility and a productive line that are shifted to a mass production system that the kinds of defect and abnormality are specified to some extent, however, upon start of the productive line, the kinds of defect cannot be specified, unknown kinds of defects appear consequently, and it is not determined that plural kinds of defect are combined, so that it is difficult to collect the sample data and the model rule, and this makes it impossible to effectively apply the inspection apparatus.

Even if the sample data of the defective product can be prepared well and the inspection apparatus can be designed, with respect to some kind of defective product, finding out a cause of generation of the defective product day by day, the productive facility and the productive line are improved so as to prevent the defective product from being generated. Therefore, this is very ineffective since the sample data are collected and the model rule is made with respect to the defective product that is not generated at pains. In addition, it takes a large amount of labor and time because it is necessary that the sample data of the defective product are collected whenever a new kind of defective product appears and an effective model rule is made on the basis of these sample data. Therefore, this involves a problem such that, when the new kind of defective product appears, the inspection apparatus cannot determine this new kind of defective product. Thus, this involves a problem such that the inspection apparatus cannot be applied effectively due to an unclear defective product such as the defective product to be eradicated and a newly generated kind of defective product or the like.

In the meantime, the facility diagnosis has the same problem. Also in the facility diagnosis, in order to diagnose the defect, it is necessary to collect a plurality of sample data of the defect and to make a model rule, and in order to diagnose the kind of defect, it is necessary to collect a plurality of sample data for each kind of the defect and to make a model rule for each kind of the defect. However, there is a transit period in the facility diagnosis, so that it is not determined that the diagnosis object becomes defective (not becomes normal) when what vibration and what sound are generated by a working machine of the diagnosis object and the productive facility itself and it is not determined that what kind of defect is generated when what kind of vibration and sound are generated at an initial status and they are not clear. It is a matter of course that a new kind of defect is generated. In other words, also in the facility diagnosis, as same as the product inspection, there are unclear defects.

SUMMARY OF THE INVENTION

The present invention has been made taking the foregoing problems into consideration and an object of which is to provide an inspection method, an inspection apparatus, and a facility diagnosis unit enabling to detect an unclear defect, capable of carrying out an appropriate inspection (diagnosis) in accordance with change of a condition of appearance of a defect (a defective manner) occurring in a transit period, and capable of being effectively used at an initial stage of the inspection.

In order to attain the above-described object, an inspection method according to the present invention is an inspection method using an inspection apparatus for extracting amount of characteristic to an inputted waveform signal and determining a status of an inspection object on the basis of the extracted amount of characteristic, the method comprising the steps of determining whether or not the status complies with a normal status by using a normal knowledge that is generated on the basis of only data of the normal status at an initial stage; and determining the status by using the normal knowledge and an abnormal kind knowledge, the abnormal kind knowledge being generated by abnormal kind on the basis of data of the abnormal status that are collected in accordance with repeat of the normal status determination.

In addition, according to the inspection method of the present invention, as a result of determination of the status by using the normal knowledge and the abnormal kind knowledge, if the abnormal kind is not detected on the basis of the abnormal kind knowledge, deleting the abnormal kind knowledge of the abnormal kind, the determination processing is carried out with the abnormal kind knowledge of the abnormal kind deleted.

In addition, the inspection apparatus according to the present invention is an inspection apparatus for extracting amount of characteristic to an inputted waveform signal and determining a status of an inspection object on the basis of the extracted amount of characteristic, having: a first mode for determining whether or not the status complies with a normal status by using a normal knowledge that is generated on the basis of only data of the normal status of the inspection object; and a second mode for determining whether or not the status is normal and whether or not the status complies with a prescribed abnormal kind by using the normal knowledge that is generated on the basis of the data of the normal status of the inspection object and an abnormal kind knowledge that is generated on the basis of data of the prescribed abnormal kind; wherein, at the initial stage when the abnormal kind is not specified, the inspection apparatus determines the status in the first mode; and the inspection apparatus determines the status in the second mode at a prescribed timing after the initial stage.

In addition, according to other aspect of the invention, the present invention provides an inspection apparatus for extracting amount of characteristic to an inputted waveform signal and determining a status of an inspection object on the basis of the extracted amount of characteristic, comprising: a normal status determining device for determining whether or not the status complies with a normal status by using a normal knowledge that is generated on the basis of only data of the normal status; and an abnormal kind determining device for determining whether or not the status complies with a prescribed abnormal kind by using an abnormal kind knowledge that is generated on the basis of data of the prescribed abnormal kind; wherein, at the initial stage when the abnormal kind is not specified, the inspection apparatus determines the status only by the normal status determining device; and the inspection apparatus determines overall the status by operating the normal status determining device and the abnormal kind determining device at a prescribed timing after the initial stage. In this case, the abnormal kind determining device may be additionally incorporated into the apparatus later after the initial stage. It is a matter of course that the abnormal kind determining device may be incorporated from the initial stage.

In an initial stage of the productive line such as start of it, the abnormality may occur, however, a case of the abnormality cannot be specified and the abnormal data of the sample for each abnormal kind for detecting the abnormality cannot be prepared because a plurality of causes acts synergistically. In addition, even if they are prepared, when there are many kinds of abnormalities, there are also many data of the sample, and this results in a large amount of labor and time in order to establish knowledge of the kind of abnormality for determination of each kind of abnormality. Then, at the initial stage, if there is a cause of abnormality, this cause is solved by improvement of the product to prevent the abnormality (defect) from occurring, so that the knowledge of the kind of abnormality that is established with efforts can be used only for a short period and then, becomes wasteful, and further, the improvement is carried out before establishment of the knowledge. Accordingly, it is difficult to prepare the conventional abnormal (defect product) data and to obtain the knowledge of the kind of abnormality such as the amount of characteristic and a determination condition or the like of each defective product so as to detect all defective products by using the inspection apparatus to determine if the product is abnormal, so that this is not impractical. Therefore, the conventional apparatus can be used only at a stability period of mass production when the defective cause (the kind of abnormality) is limited to some extent.

On the contrary, according to the present invention, differently from the above-described conventional technical idea, on the basis of "the defect that clears when the mass production becomes stable (namely, the defective product that appears only when the mass production is not stable) should not be extracted", and "a determination condition should be set on the basis of a normal product when the mass production is not stable", this idea is realized. Thereby, even at the initial stage, the normal data can be prepared, so that it is determined if the product is normal by using the normal knowledge that is generated on the basis of this normal data. This makes it possible to determine good or bad of the product since the initial stage.

Then, if the mass production becomes stable to some extent and the cause of the defective product or the like has been found, the knowledge of the kind of abnormality on the basis of the data of the kind of abnormality is prepared, and on the basis of the knowledge, it is determined if the product is included in the kind of abnormality. The status determination whether or not the product is normal is naturally carried out on the basis of the normal knowledge. Thereby, it is possible to perform an appropriate inspection in accordance with change of a status of appearance of a defect (a defective manner) occurring in the process of production (development, test of mass production, initial stage of mass production, stable period of mass production). In other words, it is possible to perform inspection from the test production stage of the inspection object. Further, since determination of the status is based on the fact if the product is normal (good) or not, it is possible to detect various defects including detection of an unclear defect of which kind cannot be specified.

Providing a dummy abnormal data generating device for generating the dummy abnormal data by processing the data of the normal status, the inspection apparatus carries out the normal status determination processing by using the dummy abnormal data that is generated by the dummy abnormal data generating device so as to enable to evaluate the normal knowledge. Particularly, upon determining the product only based on the normal knowledge, there is no abnormal sample data. Therefore, changing the normal data and generating pseudo dummy abnormal kind data (according to the embodiment, it corresponds to "the dummy NG data"), it is possible to evaluate the knowledge on the basis of this data.

Furthermore, the normal status determining device calculates a vector making plural amounts of characteristic into one unit so as to enable to decide the status on the basis of a distance between the vectors. In addition, at least one of the normal status determining device and the abnormal kind determining device calculates a vector making plural amounts of characteristic into one unit so as to enable to decide the status on the basis of a distance between the vectors. Then, a distance between the vectors can be made into a Mahalanobis distance. Thereby, the processing becomes rather simple and various kinds of the amount of characteristic can be generally determined, so that the determination can be carried out more accurately.

In addition, a threshold to determine whether or not the status is the normal status in the normal knowledge may be set at a value that a cost caused by discarding the inspection object that is determined not to be normal and a cost expensed to modify the inspection object that is determined not to be normal into normal are balanced.

In addition, a threshold to determine whether or not the status is the normal status in the normal knowledge may be set by a registration device having information of a quality function limit, discard cost information, and adjustment cost information registered therein; a loss function calculating device for calculating a loss function on the basis of the information of the registration device; and a threshold calculating device for calculating a threshold ($\Delta$) on the basis of the loss function of the loss function calculating device. In this case, the information of a quality function limit may correspond to $\Delta 0$ shown in FIG. 18 according to the embodiment, the discard cost information may correspond to A0 shown in FIG. 18 according to the embodiment, and the adjustment cost information may correspond to A shown in FIG. 18 according to the embodiment. Then, the registration device may correspond to a registration device 20*f* shown in FIG. 17 according to the embodiment.

According to the above-described setting, it is possible to prevent the product that is not necessarily discarded originally from being discarded by excess management, so that economical efficiency can be improved.

In addition, a facility diagnosis apparatus according to the present invention is a facility diagnosis unit for extracting amount of characteristic to an inputted waveform signal and determining a status of a facility on the basis of the extracted amount of characteristic, comprising: a normal status determining device for determining whether or not the status complies with a normal status by using a normal knowledge that is generated on the basis of only data of the normal status of the facility that is a diagnosis object; and an abnormal kind determining device for determining whether or not the status complies with a prescribed abnormal kind by using the abnormal kind knowledge that is generated on the basis of data of the prescribed abnormal kind; wherein, at the initial stage when the abnormal kind is not specified, the facility diagnosis unit determines the status only by the normal status determining device; and the facility diagnosis unit determines overall the status of the facility by operating the normal status determining device and the abnormal kind determining device at a prescribed timing after the initial stage.

According to the above-described each invention, "an initial stage" means a stage when at least a certain normal work is known, or a stage when normality and abnormality can be discriminated but the kind of abnormality cannot be sufficiently specified, or a stage when appearance of abnormality in an inspection object is uncertain or the like. According to the embodiment, the test or the test of mass production stage the under the status (a) shown in FIG. 3 corresponds to this.

In addition, "after that" means prescribed timing that has passed the initial stage, and may include arbitrary timings when passing the initial stage and after passing the initial stage. Then, passing the initial stage means the stage when the normality and the abnormality can be discriminated and further, the kind of abnormality can be specified. According to the embodiment, any of the initial stage of mass production or the stable stage of mass production shown in FIG. 3B may correspond to this.

According to the inspection apparatus and the inspection method according to the present invention, by determining whether or not the product is normal only on the basis of the sample data of the normal product, an unclear defect can be detected, and further, in accordance with change of the status of defect appearance (a defect status) of a transit period, it is possible to carry out a proper inspection (diagnosis). In addition, the inspection apparatus can be effectively used from the initial stage of the transit period.

BRIEF DESCRIPTION OF THE DRAWINGS

FIG. 7 shows an example of a data structure of an amount of characteristic and history database.

FIGS. 8A and 8B show an example of an inner data structure of a database for each history kind.

DESCRIPTION OF THE PREFERRED EMBODIMENTS

Figure 1:
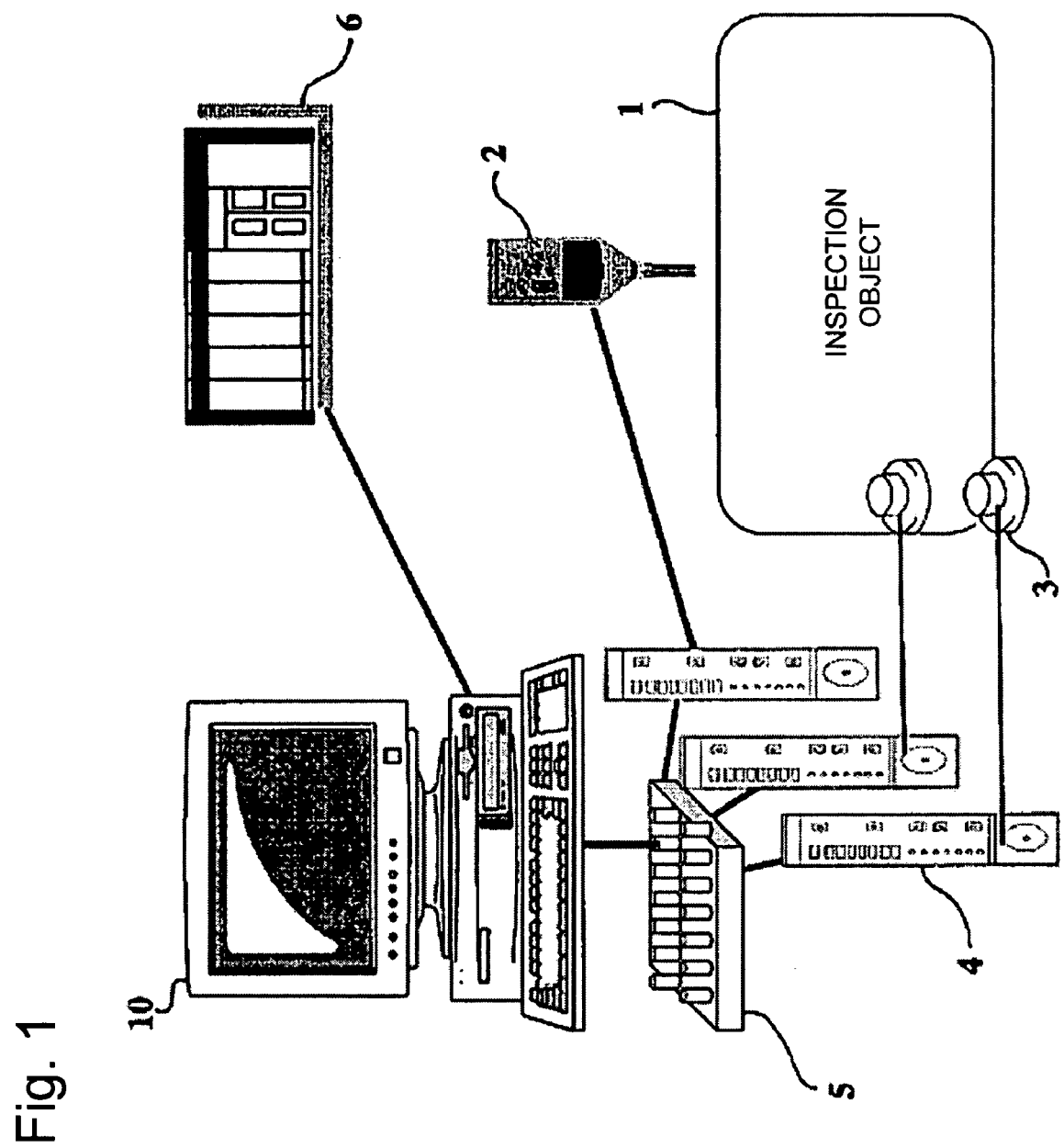
FIG. 1 shows an example of a system structure to which the present invention is applied.

FIG. 1 shows a preferred embodiment of the present invention. As shown in FIG. 1, according to the present embodiment, after amplifying signals from a microphone 2 that contacts an inspection object 1 or is arranged in the vicinity of the inspection object 1 and an acceleration pickup 3 by an amplifier 4, the digital data is changed by an AD converter 5, and then, an inspection apparatus 10 may obtain the digital data. In addition, operating timing and other data are obtained also from a PLC 6. Then, the inspection apparatus 10 may obtain waveform data on the basis of the sound data that are collected by the microphone 2, or the waveform data on the basis of the vibration data that are collected by the acceleration pickup 3, and the inspection apparatus 10 may extract the amount of characteristic from that waveform data and may determine good or bad. In the meantime, in FIG. 1, the both of the microphone 2 and the acceleration pickup 3 are arranged on the inspection object 1, however, either one of them is arranged, and the inspection apparatus 10 may correct the waveform data on the basis of either one of the sound data or the vibration data. Further, a structure of hardware of the system is basically the same as the conventional one.

According to the present invention, in the inspection apparatus 10, a basic algorithm is that a determination knowledge (rule) to be used upon determining good or bad is generated on the basis of a normal sample and the sample that complies with a condition is determined to be a normal product and the sample that does not comply with the condition is determined to be a defective product. By adopting such a structure, it is possible to carry out an appropriate good or bad determination at a stage of a transit period, and in addition, in accordance with each period of time to a stable period, it is possible to perform the appropriate good or bad determination.

Figure 2:
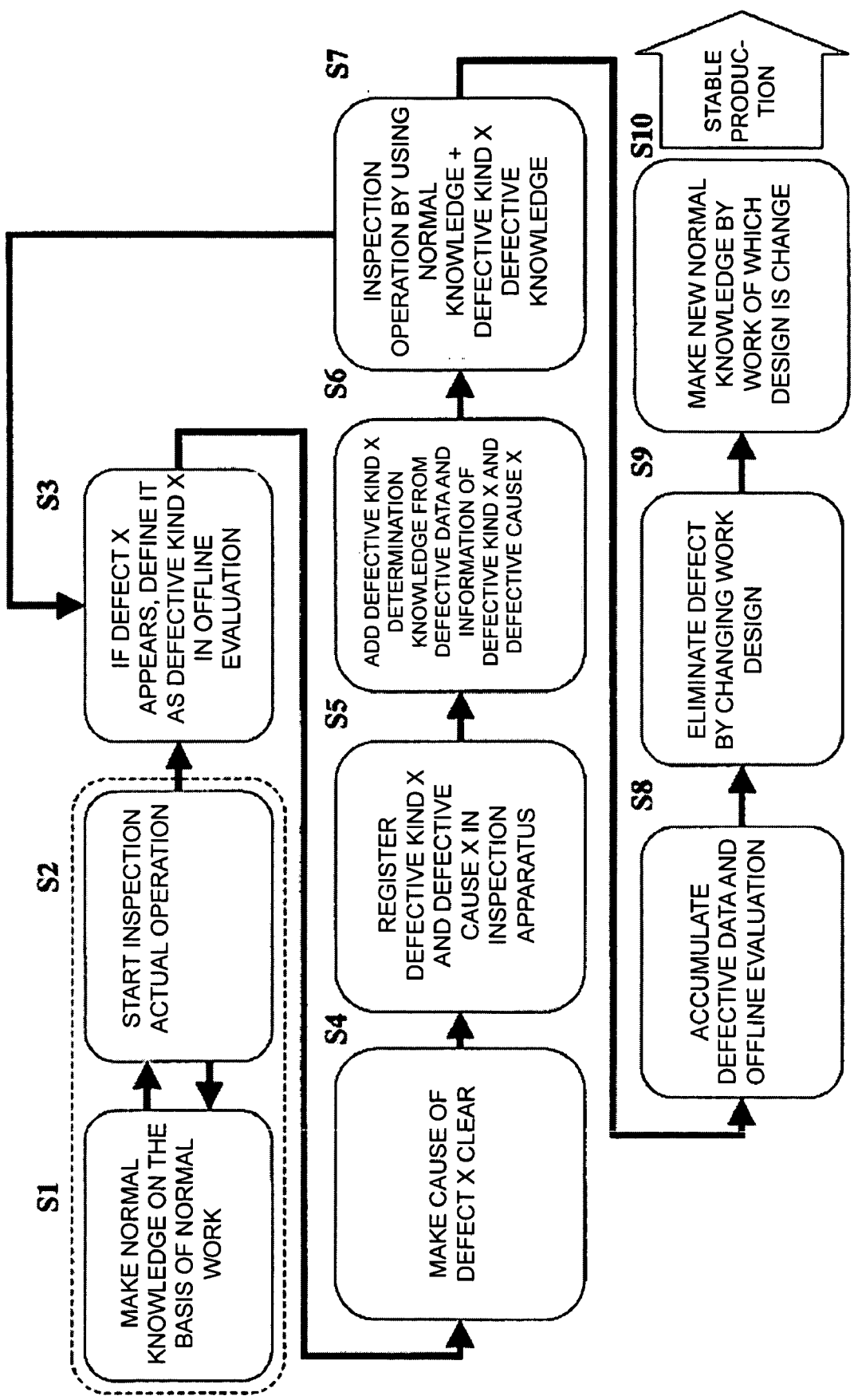
FIG. 2 shows an example of a preferred embodiment according to the present invention.

An example from the transit period to the stable period is as shown in FIG. 2. In this case, assuming a step to manufacture a product, FIG. 2 shows a flow from a test production stage, to an initial stage of mass production, and down to a stable stage of mass production. At first, when an examiner sets determination knowledge (a normal knowledge) on the basis of a normal work (a normal and good product), the inspection apparatus 10 may register the determination knowledge (S1) to start inspection actual operation (S2). In other words, since it is possible to define the normal product, setting the amount of characteristic and a determination rule or the like that are appropriate for recognizing the normal product on the basis of various waveform data (a sound and a vibration or the like) to be obtained from the normal product, the inspection apparatus 10 may store the determination knowledge. Then, the inspection apparatus 10 may determine good or bad on the basis of the normal knowledge that is stored with respect to the manufactured inspection object under the status that the operation is started in fact (S2). In addition, depending on the judgment of the examiner, adding a sample of the normal product that is obtained in accordance with this actual start of operation, the normal knowledge of the inspection apparatus 10 is adjusted according to need to change setting of the normal knowledge of the inspection apparatus 10 (S1). Thus, even if many defective products are generated in the initial stage and a defective cause and a defective kind cannot be specified, it is possible to perform good or bad determination that is proper for the transit period by using the inspection apparatus 10.

Then, repeating the above-described processing several times, some defective products are collected by increase of the sample data of the product and a defective kind can be defined by evaluating the cause (S3), the examiner makes the cause clear and the information of a defective kind X and a defective cause X are registered in the inspection apparatus 10 to be stored there (S5). The examiner creates a determination knowledge (a defective knowledge) in order to detect the defective product from the sample data on the basis of the defective product as same as the conventional case, and the inspection apparatus 10 may register the determination knowledge additionally (S6). Thereby, the inspection apparatus 10 can perform the inspection operation by using both of the normal knowledge, and the defective kind and defective knowledge (S7).

As a result, the inspection apparatus 10 inspects the product by using both of the normal determination knowledge and the defective determination knowledge for each defective kind as same as S1 and S2, so that the inspection apparatus 10 can discriminate if the status is a normal one or a defective one, and further, the inspection apparatus 10 can determine a kind of the defective status. In addition, there is a case that the taken waveform data does not comply with any condition of the defective kind determination knowledge, and in such a case, it is possible to judge that the waveform data complies with a new defective kind. Then, if a prescribed number of sample data on the basis of the new defective kind are collected, returning to S3, the inspection apparatus 10 determines a new defective kind and makes defective determination knowledge for determining the new defective kind through the steps of S4 to S6. Then, the inspection apparatus 10 may register this defective determination knowledge additionally.

In addition, at a period of time when rather many defective products are generated such as the test production stage or the initial stage of mass production, normally, the improvement of the product is appropriately carried out so as to prevent the defective product from being generated. Therefore, a generation ratio of the defective product corresponding to definitions of the defective kinds that are obtained in the step of S3 is gradually decreased, and the generation ratio of some defective kinds becomes 0. Thus, the defective product belonging to apart of the defective kind definitions intend to eliminate the defective product by changing a design and adjusting the productive facility so as to prevent generation of the same defect by performing various kinds of improvements of the product (S8, S9).

If the defective products to be eliminated by changing the design and adjusting the productive facility are increased, there is no defective product corresponding to the defective kind and the defective knowledge that have been used so far to be detected, so that the determination processing using such a defective knowledge is useless. Therefore, on the basis of a normal work after changing the design, a new normal knowledge is created (S10). Hereinafter, the inspection apparatus 10 can perform the good or bad determination by performing the determination processing by using the newest normal knowledge, and even when an unexpected defective product is generated, the inspection apparatus 10 can certainly detect the defective product. It is a matter of course that it may difficult to prevent the generation of the defective product completely even if the step of changing the design in S9 is terminated, and a defective product belonging to the known defective kind that cannot be completely eliminated may be generated. Thus, when it is known that the defective product belonging to the defective kind is generated with a low frequency, even at a stable period of mass production on and after S10, the good or bad determination may be available on the basis of a prescribed defective kind and a prescribed defective knowledge together with the normal knowledge.

Thus, since it is based on the premises that the good or bad determination is carried out on the basis of the normal knowledge, from a very initial stage such as a test stage, accurate good or bad determination can be carried out without variation depending on the inspection apparatus, and further, at each period from the test stage to the stable period of mass production, the appropriate determination processing can be carried out respectively.

FIG. 3 shows an example of variation of a determination result (a horizontal axis) and an appearance status (a vertical axis: the number of appearances) of normality/abnormality (defect) at each stage from the test stage to the stable period of mass production. In FIG. 2, focusing attention on content and a procedure to be carried out at each step, they are described, and on the basis of them, an embodiment of the present invention is explained. Here, an embodiment of the present invention will be described while citing the determination result.

Figure 3A:
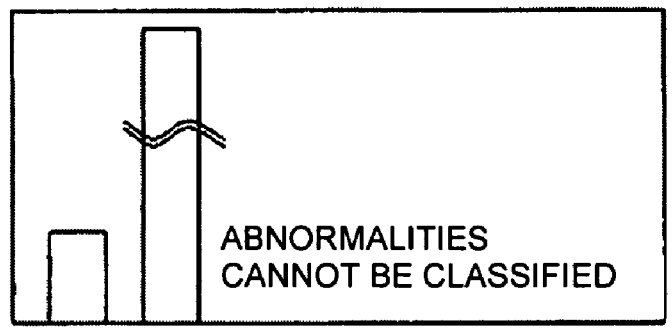
FIGS. 3A, 3B and 3C show an action and operation principle of the embodiment.

At first, FIG. 3A shows a status of the determination result at the test stage of mass production. In this transit period stage, the normal product can be defined. In addition, there are the abnormal products among the manufactured products, and it is not possible to grasp what abnormality is generated and how much the abnormality is generated. Further, the abnormality is identical with the status when many modes are generated at random, so that it is not possible to carve the kind of abnormality, so that according to a determination algorithm on the basis of the abnormal determination, even if the algorithm is made very minutely, the abnormality cannot be detected completely.

Accordingly, under such a status, generating a determination algorithm on the basis of the normal status, the good or bad determination is carried out. In other words, as shown in FIG. 3A, discrimination if the product is normal (good) or abnormal (defective) is carried out, and all of the products that cannot be normally classified are determined to be abnormal.

Figure 3B:
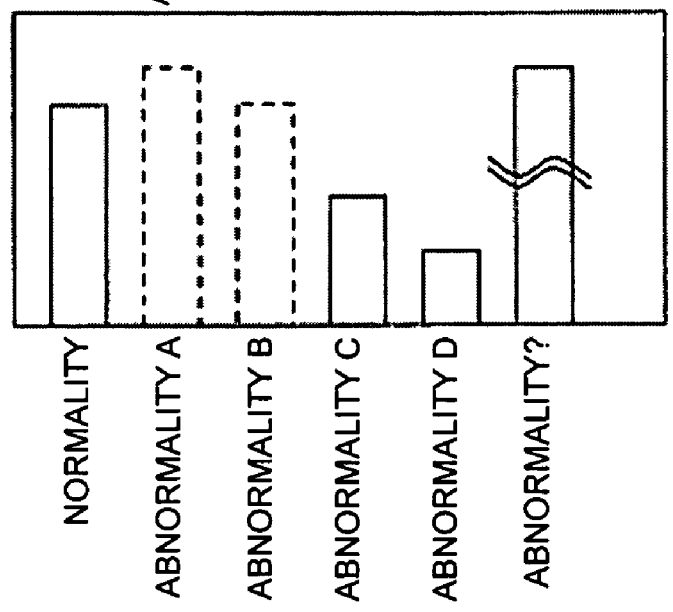

FIG. 3B shows an initial stage of mass production. Making a transition to this stage, many sample data of the normal product that have been collected so far are collected, so that a definition of the normal product becomes clearer. Further, under this status, there is a product of which abnormal kind can be clearly defined (the abnormalities A, B, C, and D) and the product of which abnormal kind cannot be clearly defined (the abnormalities ?). Therefore, with respect to the product of which abnormal kind can be clearly defined, an abnormal kind determination algorithm (the defective kind and defective knowledge) is registered in the inspection apparatus 10. Then, the inspection apparatus 10 may start the operation to carry out the determination combining both of the normal detection and the abnormal kind detection.

Further, various abnormalities are differentiated into those not appearing due to improvement (the abnormalities A, B) and those continuously appearing (the abnormalities C, D). In other words, causes of the abnormality depend on a quality of the assembling work, a quality of processing, and an original quality of design. Then, since the quality of the assembling work is improved due to the skilled operation and improvement of tools and the improved quality is maintained, generation of the defective product due to this cause is prevented. In addition, since the quality of processing is improved due to the skilled processing and stabilization of a processing machine and the improved quality is maintained, generation of the defective product due to this cause is also prevented. In the same way, since the quality of the defective product in the design quality is improved due to change of the design, generation of the defective product due to this cause is also prevented. Accordingly, in the above-described process, among the abnormal kinds, some do not appear anymore in accordance with improvement. However, the above-described improvements do not always effectively act on the entire defective products at once, and one improvement may cause another problem and a new abnormal kind may be generated.

Accordingly, the examiner checks a generation status of an abnormality (defect) at appropriate timing, and when a new abnormal kind is generated, the inspection apparatus 10 creates a determination algorithm for detecting it. Then, the inspection apparatus 10 registers the inspection apparatus 10 and also carries out determination. In the meantime, since many abnormal kinds (defective kinds) are eliminated by improvement, there is no need for the inspection apparatus 10 to always store the determination algorithms on the basis of all abnormal kinds. However, with respect to the abnormal kind that the defective product is generated despite improvement, the inspection apparatus 10 may store the determination algorithm (the defective knowledge) on the basis of that abnormal kind. The examiner collects the data such as occurrence frequency of that abnormal kind and a condition of generation or the like by using the inspection result of the inspection apparatus 10 to be prepared for change of design or the like.

Figure 3C:
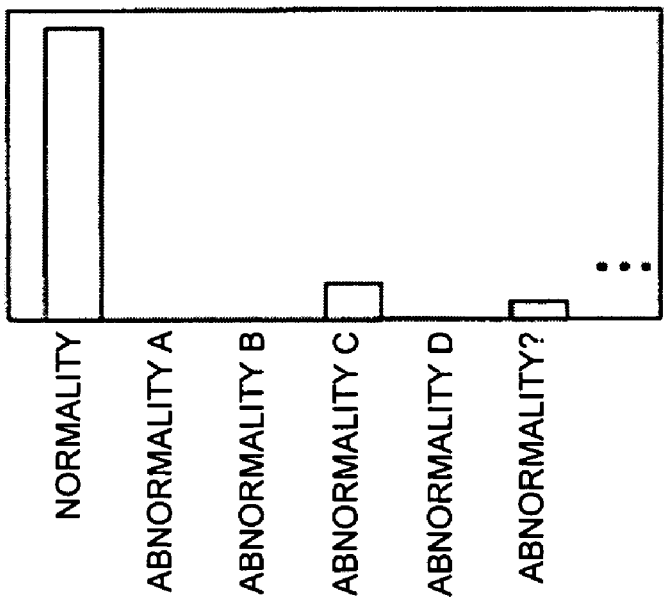

FIG. 3C shows a stable period of mass production. Moving to this stage, a definition of a normal product is made clear and distribution thereof becomes even. Further, the abnormal kind continuously appearing can be specified, a ratio of appearing becomes the minimum, and the distribution for each abnormal kind becomes even (the abnormality C). However, the unexpected abnormality (the abnormality ?) is occasionally generated.

Therefore, the inspection apparatus 10 operates the abnormal kinds by combining two determinations, namely, the normal determination and the abnormal determination. In the determination of the abnormal kind, the inspection apparatus 10 mainly operates "the abnormal kind (the abnormality C)" remaining at last and "the abnormal other" occurring at random. The random abnormality may be reappearance of the abnormal kind that has not been generated due to the improvement of the abnormal kind that was defined in the past. In the meantime, if "the abnormal other" cannot be defined, the inspection apparatus 10 judges the product that is not normal and is not the abnormal kind C as "the abnormal other" (the abnormality ?).

Figure 4A:
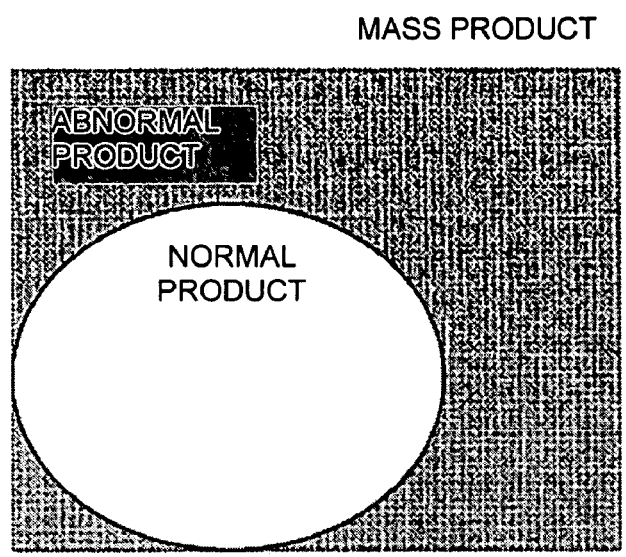
FIGS. 4A and 4B show an action and operation principle of the embodiment.
Figure 4B:
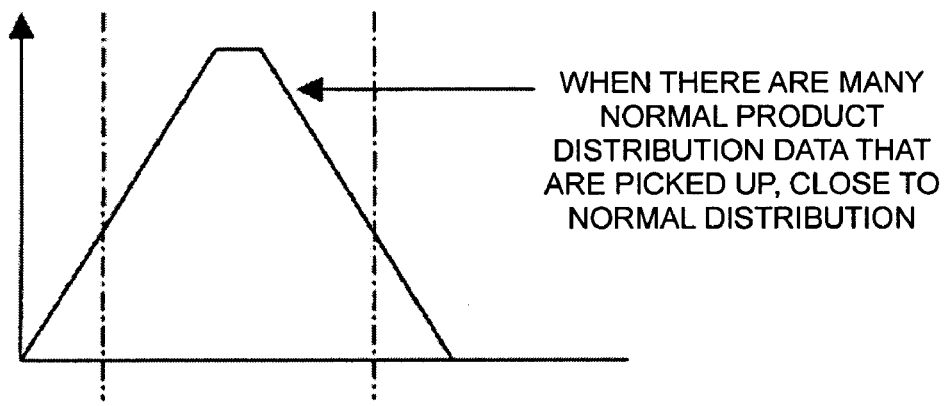
Figure 5A:
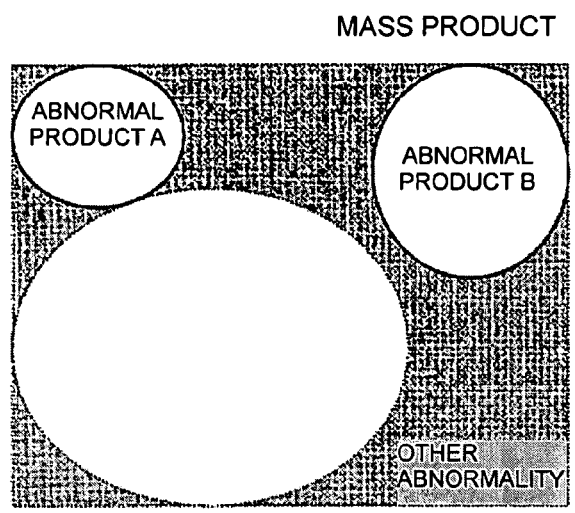
FIGS. 5A and 5B show an action and operation principle of the embodiment.
Figure 5B:
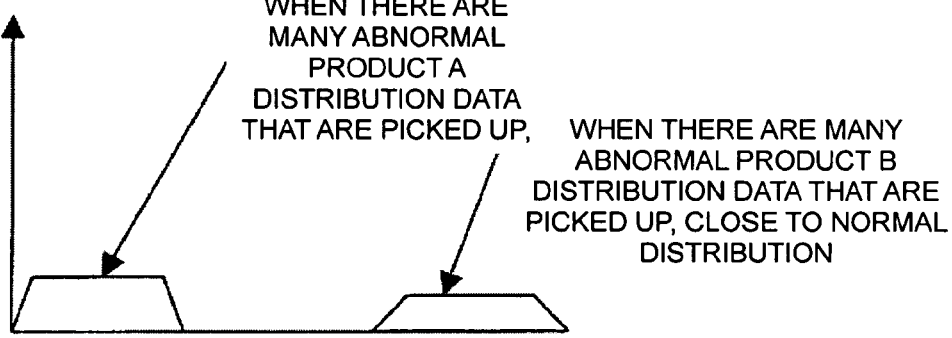

FIG. 4 and FIG. 5 are explanatory views of an embodiment focusing attention on the determination method. In other words, at first, as shown in FIG. 4, the inspection apparatus 10 may determine the normal product. In many cases, although the samples of the abnormal and defective product cannot be prepared, the sample of the normal product can be prepared, so that the inspection apparatus 10 may store the determination algorithm (the normal knowledge) that is created for detecting the normal product on the basis of that sample of the normal product. Then, only extracting the normal product by the determination algorithm from among the products manufactured by the mass production and determining remaining as an abnormal product (mass production, normal product=abnormal product). Thereby, it is possible to capture an unknown abnormal product.

In the next place, if the abnormal product appears as shown in FIG. 5, the examiner and an industrial engineer makes clear an abnormal kind X by analyzing symptom and causes (a part of the improvement activity). Then, the inspection apparatus 10 may pick up the abnormal product of which abnormal kind is known (in FIG. 5, "the abnormal product A", "the abnormal product B"), and then, the inspection apparatus 10 may treat remaining as an unknown product, namely, "the abnormal other" (the abnormal product, the abnormal product A, the abnormal product B , , , =the abnormal other). If an operation period of a line is made longer, the number of the abnormal kind is increased, however, as described in each embodiment, there are many abnormal products are not generated due to improvement of the product.

Figure 6:
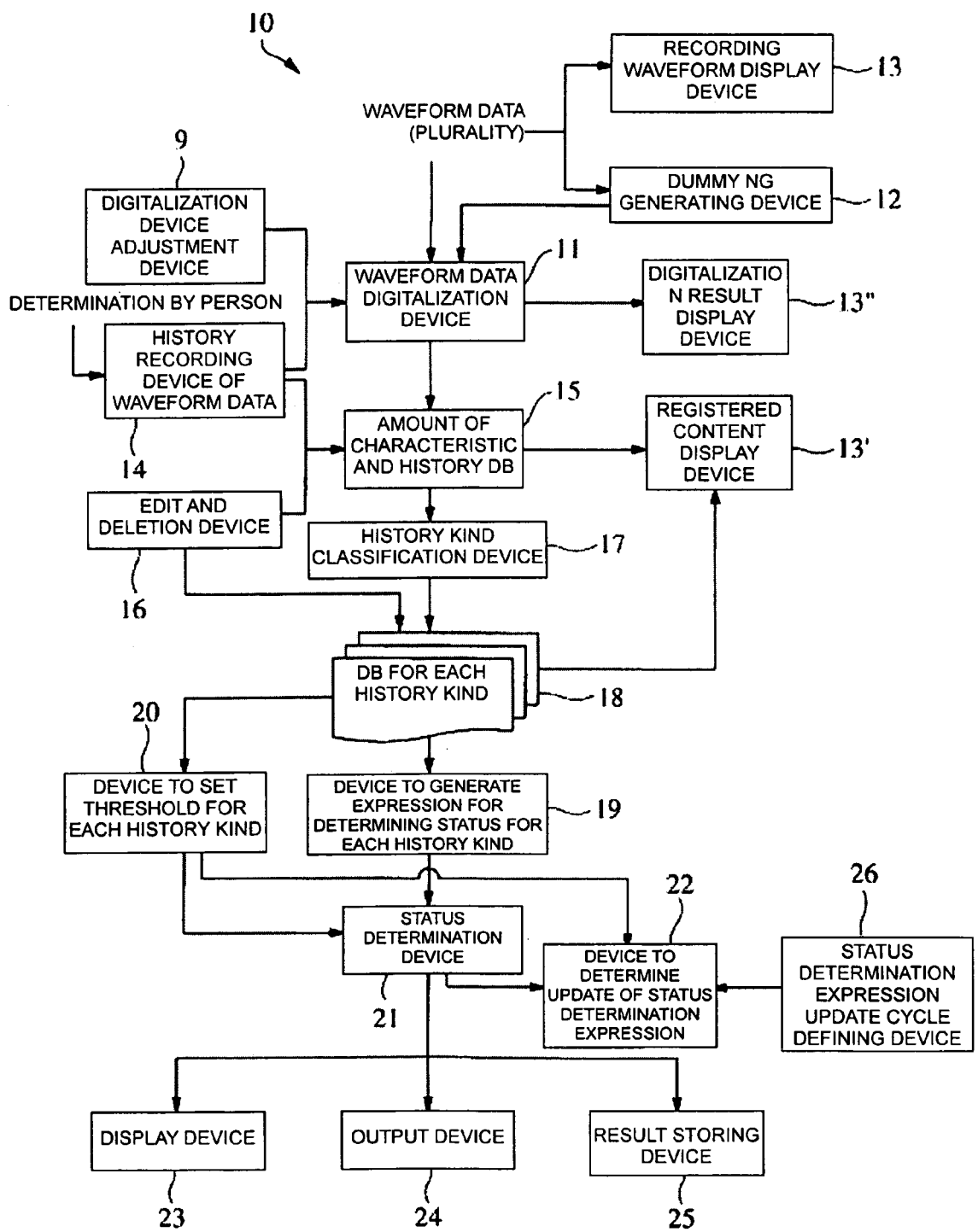
FIG. 6 shows a block diagram of a first embodiment of an inspection apparatus (when making an algorithm) according to the present invention.

In the next place, a specific inner structure of the inspection apparatus 10 for practicing the above-described various embodiments will be described below. FIG. 6 shows a function block for making a determination algorithm. The inspection apparatus 10 obtains the waveform data by various measurement instruments that are arranged in an inspection object work 1 (not illustrated). Since the waveform data is obtained for each inspection object work, the inspection apparatus 10 treats a plurality of waveform data.

As the inspection object work 1, for example, an engine of an automobile is available. Starting the engine actually, the operation of the engine is continued during the inspection period. For example, the measurement instrument is the microphone 2 and the acceleration pickup 3 in FIG. 1. The driving information collected by the inspection apparatus 10 is made into the waveform data on the basis of a sound signal in the case of the microphone 2, and the driving information collected by the inspection apparatus 10 is made into the waveform data on the basis of the vibration in the case of the acceleration pickup 3.

Operating the inspection object work 1, the waveform data that is obtained by the measurement instrument is given to a waveform data digitalization device 11, a dummy NG generating device 12, and a recording waveform display device 13. The waveform data digitalization device 11 may digitalize the waveform data that is obtained as described later and make it into the amount of characteristic.

In addition, the dummy NG generating device 12 may modify the waveform data of a normal history. Then, the dummy NG data that is created by this dummy NG generating device 12 is given to the waveform data digitalization device 11. According to the present embodiment, the sample data of the normal product can be obtained, however, the sample data (the NG data) of the defective product (abnormality) cannot be always obtained. Therefore, the dummy NG generating device 12 takes into the sample data (the waveform data) of the normal product to create pseudo NG data on the basis of the normal waveform data of that normal product. The dummy NG data that is created in this way can be used for evaluation of the created determination algorithm. In other words, the dummy NG generating device 12 may give the dummy NG data to each device of a later chapter, and as a result of determination of the product on the basis of the dummy NG data, it is possible to estimate the accuracy of a created recognition algorithm depending on whether or not the abnormality can be accurately determined.

The recording waveform display device 13 may display the waveform data that is taken into from the measurement instrument or the recording waveform data that is stored in the recording device. The inspection apparatus 10 can be configured by a general-purpose personal computer, so that the recording waveform display device 13 can be realized by a display monitor that is provided to the personal computer.

In addition, a digitalization device adjustment device 9 and a history recording device 14 of the waveform data are connected to the waveform data digitalization device 11. Upon extracting the amount of characteristic, the digitalization device adjustment device 9 may perform parameter adjustment of that the amount of characteristic and the digitalization device adjustment device 9 has a function to give an instruction of the parameter adjustment to the waveform data digitalization device 11. An operating material (person) may determine normal/abnormal (in the case of abnormal, further, determine the abnormal kind) from a sound generated when driving the above-described inspection object work 1 and the history recording device 14 of the waveform data may record its determination result therein. Further, the waveform data digitalization device 11 can output and display the waveform data digitalization result, namely, the obtained each amount of characteristic to the recording waveform display device 13".

The waveform data digitalization device 11 may extract a prescribed amount of characteristic from the given waveform data. As the amount of characteristic to be extracted, in addition to an RMS (Route mean Square Value) indicating a size of a vibration level, an XP indicating the average value of the data to the upper nth data of the vibration level in the data in one frame, and an AMXa indicating the average value to the upper nth data of a change amount of the data in one frame, various characteristics can be used. Such amount of characteristic can be obtained for each inspection object work. Then, relating the determination result (history) that is obtained by the history recording device 14 of the waveform data to the amount of characteristic that is obtained by the waveform data digitalization device 11, both of them is stored in the an amount of characteristic and history database 15. In this case, the amount of characteristic and the history are tagged with an experiment No. and are stored.

An example of a data structure of this amount of characteristic and history database 15 is as shown in FIG. 7. The experiment No. is a kind of record number and it is a number that is set as a matter of convenience for each inspection object work. Simply, the experiment No. is set to be aimed at in the order of inspection. Then, in a column of the history (normality/abnormality (including the abnormal kind), the data that is given from the history recording device 14 of the waveform data is stored, and in a column of amount of characteristic hereinafter, each amount of characteristic that is given from the waveform data digitalization device 11 is stored.

In the meantime, the data that is stored in the amount of characteristic and history data base 15 can be displayed on a registered content display device 13' or this data can be changed by operating an edit and deletion device 16. The registered content display device 13' in this case and the above-described recording waveform display device 13 can be physically realized by the same monitor.

In addition, the data that is stored in the amount of characteristic and history database 15 is called up by a history kind classification device 17 and the data is classified based on the history information. Then, the history kind classification device 17 may create the database for each history kind. In addition, the created database is stored in a database for each history kind 18. In this case, the history kind is classified not only by normal and abnormal, and when it is abnormal, the data is classified for each abnormal kind. In addition, the abnormal kind that cannot be specified is regarded as other (abnormal). Then, an example of an inner data structure of this the database for each history kind 18 is as shown in FIG. 8. FIG. 8A shows the data of normal, and FIG. 8B shows the data of abnormal.

Then, the data that is stored in this database for each history kind 18 is outputted to the registered content display device 13' and is displayed on the registered content display device 13'. In addition, the edit and deletion device 16 can delete and change the data that is stored in the database for each history kind 18.

Each data that is recorded in this database for each history kind 18 is given to a device to generate an expression for determining a status for each history kind 19 in a next chapter for each history kind. This device to generate a status determination expression for determining a status for each history kind 19 may generate a status determination expression for determining whether or not the waveform data (the amount of characteristic) of the inspection object complies with each history information on the basis of the amount of characteristic for each history kind. In other words, while the device to generate an expression for determining a status for each history kind 19 generates a status determination expression for determining normality on the basis of the normal data having the normal history kind, the device to generate an expression for determining a status for each history kind 19 generates a status determination expression for determining the abnormality A on the basis of the abnormal data (the data of the abnormal product A) having the abnormal history kind. Then, the generated status determination expression is given to a status determination device 21 in a next chapter.

In the meantime, as the status determination expression, various systems such as a Mahalanobis distance system, an Euclidean distance, a normal/abnormal contrast system, a neural network system, and a fuzzy system using a membership function or the like are available. Then, as described later, the status determination expression can be automatically created and as same as the conventional case, a person can make it.

In the case of the present invention, at first, a status determination device 21 determines the data only on the basis of the normal knowledge, so that the data having the "normal" history is only stored in the amount of characteristic and history data base 15, and also in the database for each history kind 18, the data having the "normal" history kind shown in FIG. 7 is only generated and stored. Therefore, also in the device to generate an expression for determining a status for each history kind 19, a status determination expression for determining normality is generated, and the status determination expression is set in the status determination device 21.

In addition, each data recorded in the database for each history kind 18 is also given to a device to set a threshold for each history kind 20. Then, this device to set a threshold for each history kind 20 may decide a threshold for discriminating if a result obtained by calculating the amount of characteristic that is obtained on the basis of the waveform data obtained from the inspection object work by using the status determination expression complies with its history kind. Then, the decided threshold is given to the status determination device 21.

Thereby, a determination algorithm and normal knowledge and an abnormal kind determination algorithm (a defective kind and a defective knowledge) are generated, and the status determination device 21 may carry out bad or good determination on the basis of the waveform data (the amount of characteristic) of the given inspection object by using the set status determination expression and the set threshold. Then, its determination result is outputted via a display device 23 and an output device 24 to be stored in a result storing device 25. In the result storing device 25, not only the status determination result but also a determination (history) carried by the person, the waveform data, and the amount of characteristic or the like are stored with related each other. In addition, the display device 23 is physically the same as the recording waveform display device 13 or the like.

In the meantime, at first, the normal determination is only carried out, however, if the inspection has been continuously carried out and the defective product (abnormal) data are collected to some extent, the device to generate an expression for determining a status for each history kind 19 may generate the database for each history kind 18 with respect to the abnormal kinds of abnormalities A, B , , , and a status determination expression for the abnormalities A, B , , , ; and the status determination device 21 may additionally set that status determination expression. In addition, by accumulating not only the abnormal data but also the normal data in this way, there is a possibility of creating a better status determination expression. Therefore, comparing a new status determination expression created on the basis of the currently accumulated data with the currently using status determination expression, a device to determine update of a status determination expression 22 may determine which of them is better. If the device to determine update of a status determination expression 22 judges that the newly created status determination expression is better, the device to determine update of a status determination expression 22 may display its result on the display device and may inquire of a user whether or not the status determination expression can be updated. Then, when the user inputs that the status determination expression can be updated to allow the update, the status determination device 21 may update the status determination expression into a new one by the device to determine update of a status determination expression 22. In addition, the automatic update is also available without inquiring of the user.

Then, the device to determine update of a status determination expression 22 may determine good or bad determination of update at an update cycle that is defined by a status determination expression update cycle defining device 26. In the meantime, as the update cycle definition, various update cycles such as a time when a prescribed number of the sample data are stored and a prescribed period of time or the like can be defined.

Figure 9:
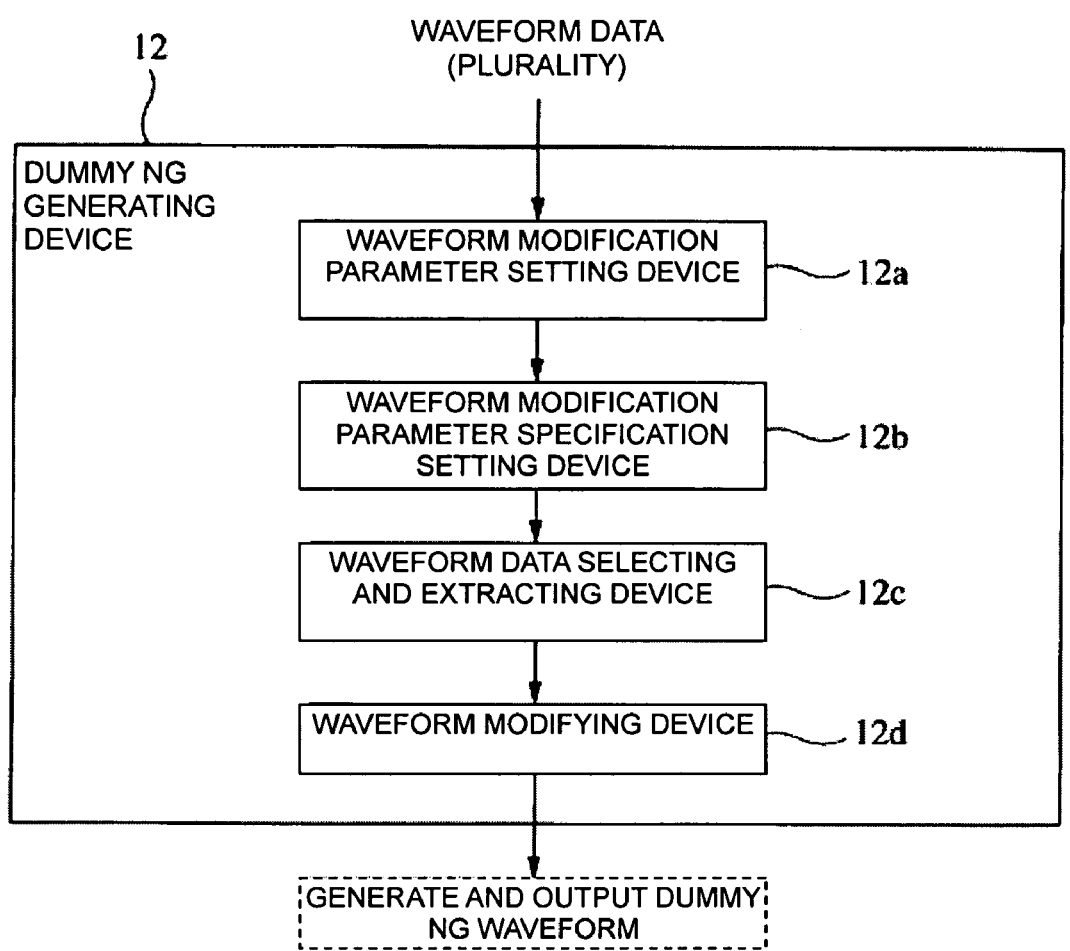
FIG. 9 shows an inner structure of a dummy NG generating device.

In the next place, each processing part will be described in detail below. At first, as shown in FIG. 9, the dummy NG generating device 12 is provided with a waveform modification parameter setting device 12a at its input side and sets a parameter for modification with respect to the inputted waveform data.

A specification example to be set may include (1) an abnormal mode waveform synthesis of a waveform library (synthesis of a bias core abnormal waveform, synthesis of an impact waveform), (2) n-dimensional amplitude of a driving condition specific frequency (a rotation frequency, 1.5 times as the 1 to 4-dimensional amplitude of an engagement frequency), (3) a specific or a random frequency amplitude (1.2 times as the amplitude of a frequency of 500 to 1,000 Hz), (4) an FM modulation, an AM modulation, and (5) a phase deviation (slightly deviate an original waveform phase and combine it with the original waveform) or the like.

In this case, in the waveform synthesis of (1), by synthesizing an abnormal waveform that is not generated in the normal waveform, the synthesized waveform data appears as a waveform data that is different from the normal data at an overlapped portion due to an influence of that synthesized abnormal waveform portion to be the abnormal data. In addition, in (2), for example, assuming a gear or the like, a sound and a vibration that are generated by the engagement frequency at abnormality appear at a specific frequency. This engagement frequency can be calculated by the number of gears and a rotation frequency. Therefore, by increasing the n-dimensional amplitude of each frequency (by increasing a power of the normal product), the waveform data becomes the abnormal data that is different from the normal data. Although the detailed explanation is omitted, in the other case, it is possible to generate the waveform data that cannot be obtained normally.

The set parameter is given to a waveform modification parameter specification setting device 12b at a next chapter together with the waveform data. This waveform modification parameter specification setting device 12b sets a specification to modify a waveform modification parameter on the basis of an experiment plan direct run list. For example, with respect to the waveform synthesis, there is a parameter of "two levels of ON/off"; with respect to the specific frequency, there is a parameter of "three levels of a frequency"; and with respect to the amplitude, there is a parameter of "three levels of 1.2 times, 1.5 times, and two times". Thus, a value or the like of each parameter upon modifying a waveform or the like is set.

Then, a waveform data selecting and extracting device 12c may select the waveform data by the number of the experiment No. in the direct run list at random. Further, a waveform modifying device 12d may change the waveform data in accordance with the modification amount that is selected in a modification parameter specification on the basis of the direct run list. Thereby, at last, the dummy NG waveform is generated, and the generated dummy NG waveform that is normal as the waveform data is added to the waveform data. In other words, if the good or bad determination can be also carried out on the basis of this waveform data and the product can be determined as the defective one, a reliability of the inspection algorithm of the inspection apparatus 10 can be improved.

The waveform data digitalization device 11 may receive the waveform data that is obtained from the inspection object to be given from the measurement instrument, and the dummy NG data to be given from the dummy NG generating device 12 (the waveform data that is generated in a pseudo manner to be determined as a defective product) and may extract the amount of characteristic from each waveform data. As the specific amount of characteristic extracting algorithm, conventional various algorithms are available, and further, other amount of characteristic extracting algorithm is also available.

Figure 10:
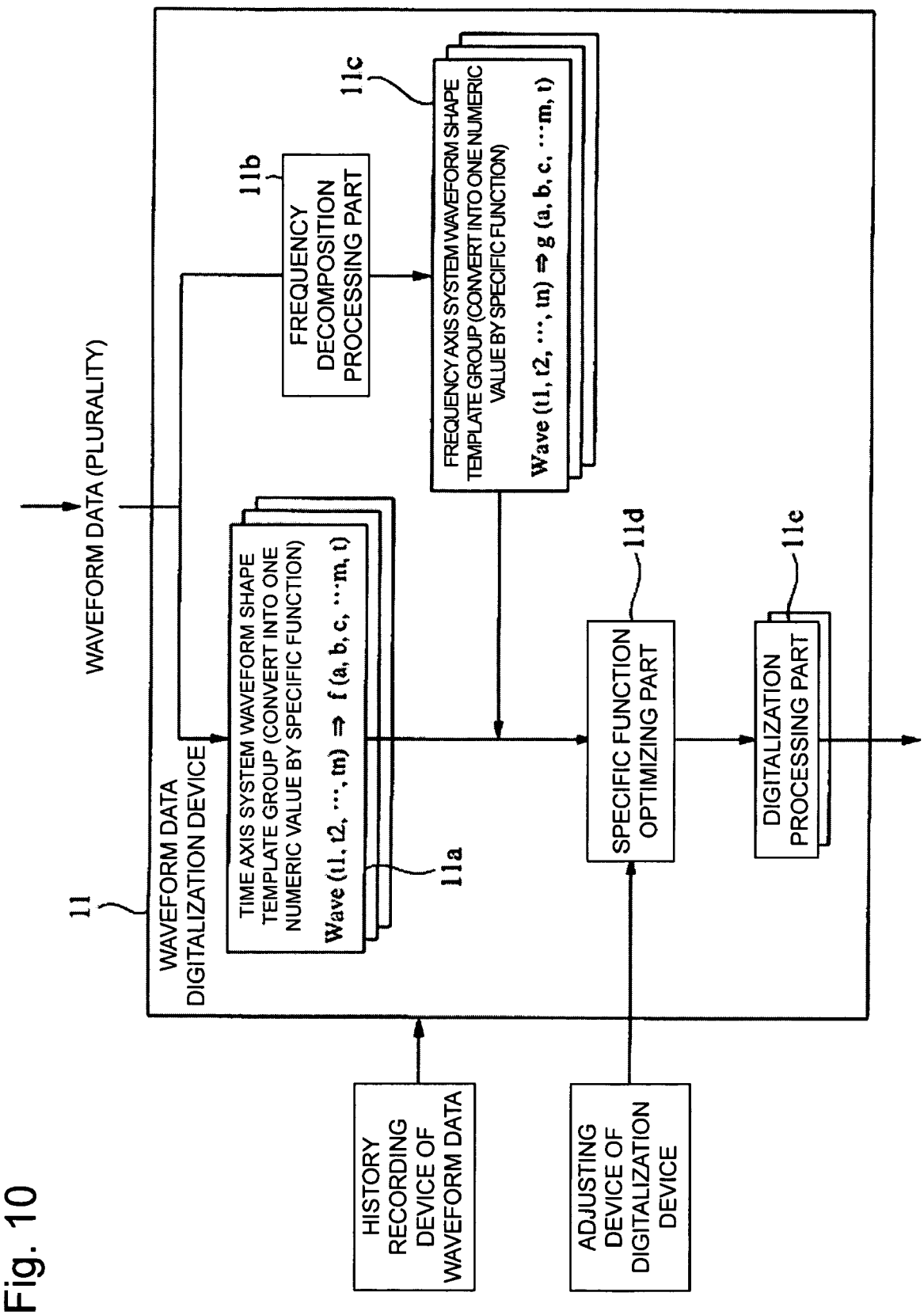
FIG. 10 shows an inner structure of a waveform data digitalization device.

As an example, the waveform data digitalization device 11 is configured as shown in FIG. 10. The waveform data obtained from the measurement instrument is stored with divided into a time axis system waveform shape template group 11a and a frequency axis system waveform shape template group 11c that is obtained by performing frequency decomposition such as FFT and order conversion or the like by device of a frequency decomposition processing part 11b. The data to be registered in each template group is basically the same as the conventional case, and from one waveform data, plural kinds of data of the amount of characteristic are extracted. Various amounts of characteristic are obtained from specific functions respectively. The corresponding amount of characteristic extracting processing algorithm will be briefly described below. The waveform data digitalization device 11 carves out the data for a time necessary for calculation from the waveform data of all times that are sampled, and further, making one unit of data obtained by dividing the carved out data with a prescribed number of data into one frame, the waveform data digitalization device 11 extracts the amounts of characteristic of plural kinds (for example, 40 kinds) in one frame. Then, with respect to each amount of characteristic obtained from all frames, for each amount of characteristic of the same kind, a calculated value of a typical characteristic amount is obtained according to an average method and other various methods. Therefore, the waveform data digitalization device 11 may calculate plural pieces (40 kinds) of the calculated value of a typical amount of characteristic in accordance with the kind of the amount of characteristic.

In the meantime, items that the waveform data digitalization device 11 obtains from the specific function are decided in advance, for example, an average value, the maximum value, and an average of the upper n pieces or the like (although the items may be added according to need), and a specific function (an arithmetic expression) for obtaining their amounts of characteristic includes an adjustable parameter (a coefficient and a constant) and by setting the parameter appropriately, the accuracy of good or bad determination is improved. In other words, if the adjustment is not appropriate, the accuracy of good or bad determination is deteriorated. Conventionally, the skilled examiner adjusts the setting of the parameter by try and error and finally, the examiner decides the parameter. In the present invention, it is a matter of course that the parameter is set by adjusting the parameter by the manual operation as same as the conventional case, however, according to the present embodiment, the inspection apparatus 10 automatically optimizes the parameter, and by using the specific function that is specified at the optimum value, the waveform data is digitalized (namely, the amount of characteristic is extracted).

Figure 11:
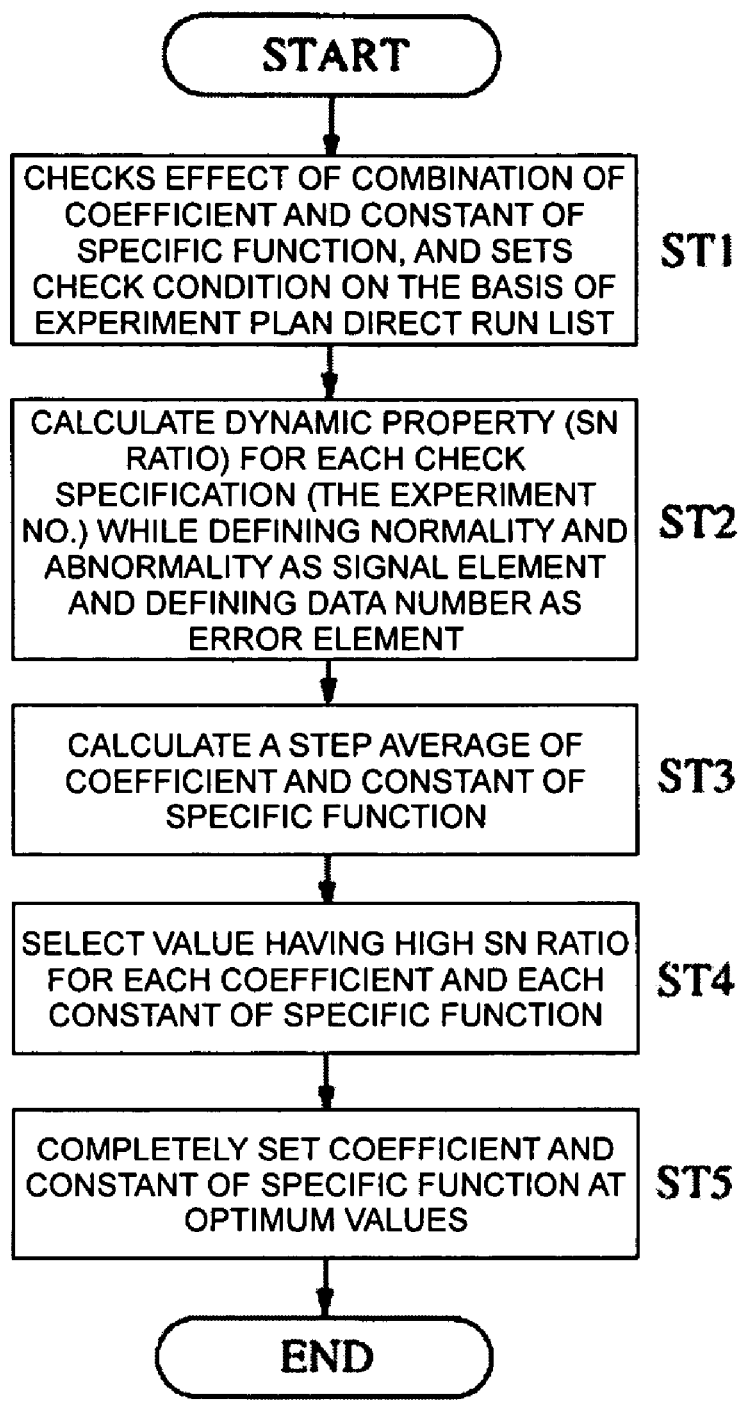
FIG. 11 shows a flow chart showing a function of a specific function optimizing part.

Specifically, the waveform data digitalization device 11 is provided with a specific function optimizing part 11d that adjusts and optimizes the specific function to be used upon digitalizing the waveform data. This specific function optimizing part 11d may change various parameters of the specific function by an instruction from the digitalization device adjustment device 9. Specifically, the specific function optimizing part 11d has a function to practice the flow chart shown in FIG. 11.

In other words, at first, the specific function optimizing part 11d checks an effect of a combination of a coefficient and a constant of the specific function, and sets a check condition on the basis of the experiment plan direct run list (ST 1). In other words, in accordance with the instruction from the digitalization device adjustment device 9, the specific function optimizing part 11d sets the combination of the coefficient and the constant as plural patterns to create the direct run list with correlated with the check condition (a check specification). Consequently, the specific function optimizing part 11d may calculate a dynamic property (sn ratio) for each check specification (the experiment No.) while defining normality and abnormality as a signal element and defining the data number as an error element (ST 2). In other words, the specific function optimizing part 11d may digitalize (obtain the amount of characteristic) plural pieces of waveform data that are given by using the specific function that is set by a parameter (a coefficient and a constant) that is defined by each check specification to obtain a distance between a group of the amount of characteristic (a numeric value) indicating OK (normality, a normal product) and a group of the amount of characteristic (a numeric value) indicating NG (abnormality, a defective product) or the like.

Then, the specific function optimizing part 11d may calculate a step average of the coefficient and the constant of the specific function (ST3), and may select a value having a high sn ratio for each coefficient and each constant of the specific function (ST4). Due to this selected value, a parameter of the specific function (a coefficient and a constant) is decided, and the specific function using the coefficient and the coefficient is set as the optimum one (ST5). Evaluation and setting of the above-described parameter of the amount of characteristic are carried out for each function, namely, for each amount of characteristic.

In addition, the specific function optimizing part 11d may give the optimized specific function to a digitalization processing part 11e. Then, the digitalization processing part 11e may digitalize the waveform data by using each optimum specific function that is set and may output the obtained amount of characteristic. The history recording device 14 may store this outputted amount of characteristic therein.

Figure 12:
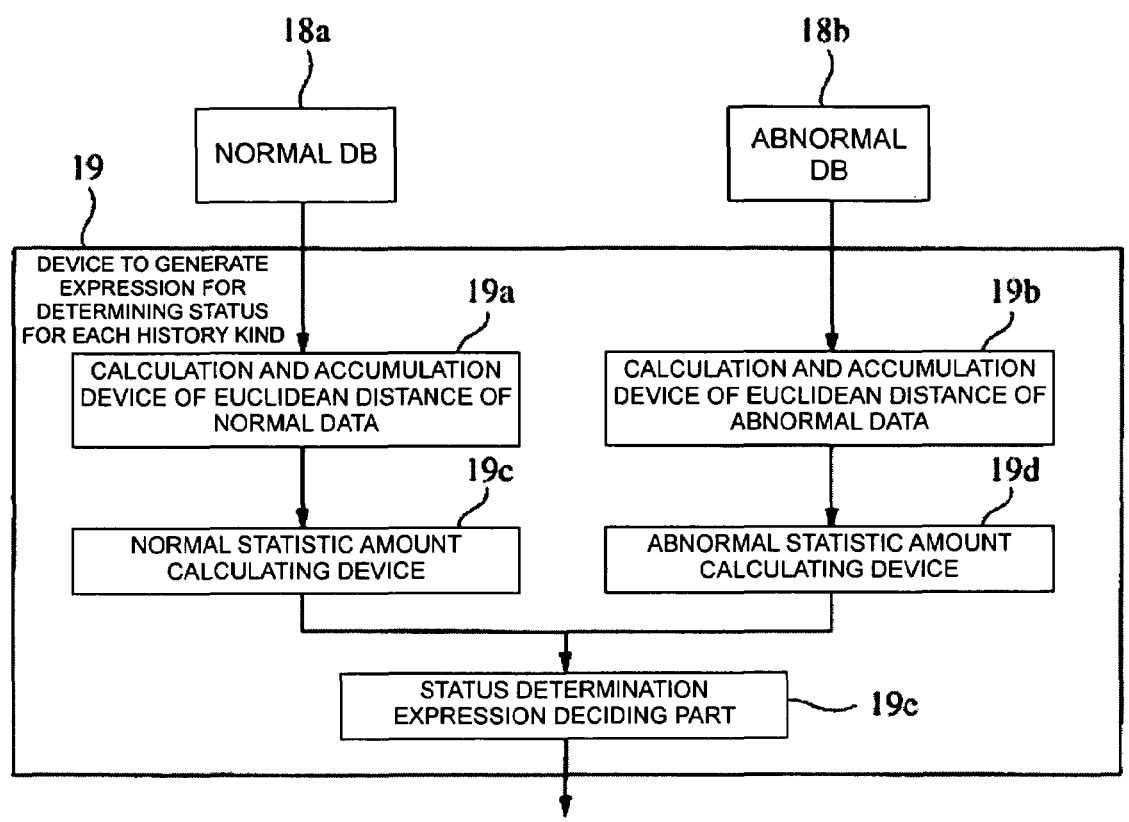
FIG. 12 shows a block diagram showing an example of an inner structure of a device to generate a determination calculating expression for determining a status for each history kind.

The device to generate an expression for determining a status for each history kind 19 can adopt various systems as described above. As an example, the inner structure shown in FIG. 12 is available. This illustrated inner structure is an example of realizing a Euclidean distance. At first, the data of the amount of characteristic for each history kind that is stored in a normal database 18a and an abnormal database 18b of a database for each history kind 18 is given to corresponding calculation and accumulation devices 19a and 19b of the Euclidean distance, respectively. The calculation and accumulation devices 19a and 19b of the Euclidean distance may obtain the Euclidean distance and may accumulate it by calculating a root of sum of squares of the amount of characteristic on the basis of the obtained normal data (the amount of characteristic). In addition, the calculation and accumulation device 19b of the Euclidean distance of the abnormal data may obtain the Euclidean distance of the normal data except for a case that the data of the processing object is the abnormal data and may accumulate it. In addition, in the case that the abnormal data is divided for each abnormal kind, the calculation and accumulation device 19b of the Euclidean distance of the abnormal data may obtain the Euclidean distance for each abnormal kind and may accumulate it.

The Euclidean distance of each data that is calculated and accumulated as described above is given to corresponding statistic amount calculating devices 19c and 19d, respectively. The normal statistic amount calculating device 19c for calculating the statistic amount of the normal data Euclidean distance may calculate a statistic amount such as the maximum value, the average value, and the standard deviation value or the like of the Euclidean distance of the given plural pieces of normal data. In the same way, the abnormal statistic amount calculating device 19d for calculating the statistic amount of the abnormal data Euclidean distance may calculate a statistic amount such as the maximum value, the average value, and the standard deviation value or the like of the Euclidean distance of the given plural pieces of abnormal data. In this case, it may obtain the Euclidean distance for each abnormal kind.

Then, the statistic amounts that are obtained by respective statistic amount calculating devices 19c and 19d are given to a status determination expression deciding part 19e at a next chapter. As comparing the maximum value of the normal statistic amount (the normal maximum value) that is obtained by the normal statistic amount calculating device 19c and the minimum value of the abnormal statistic amount (the abnormal minimum value) that is obtained by the abnormal statistic amount calculating device 19d, the status determination expression deciding part 19e may determine if the normal maximum value<the abnormal minimum value. Then, if the statistic amount is provided with the above conditional expression, the status determination expression deciding part 19e may determine that the expression obtaining the Euclidean distance of the amount of characteristic that is set is correct and may set this expression in the status determining device. Thereby, the status determination device 21 may calculate the Euclidean distance by obtaining a square root of a sum of squares of the given amount of characteristic.

In addition, if the statistic amount is not provided with the above conditional expression, setting of the specific function calculating the amount of characteristic is defined as improper, so that the status determination expression deciding part 19e requires changing of the parameter (the coefficient and the constant of the specific function) from the digitalization device adjustment device 9. Receiving this, the digitalization device adjustment device 9 may set a value other than the coefficient and the constant of the specific function that is set at a previous time. Thereby, the specific function is changed, so that the amount of characteristic that is digitalized on the basis of the changed specific function is changed, and the statistic value is also changed. By repeatedly carrying out this processing, the status determination expression deciding part 19e generates the statistic amount that is provided with the condition.

Figure 13:
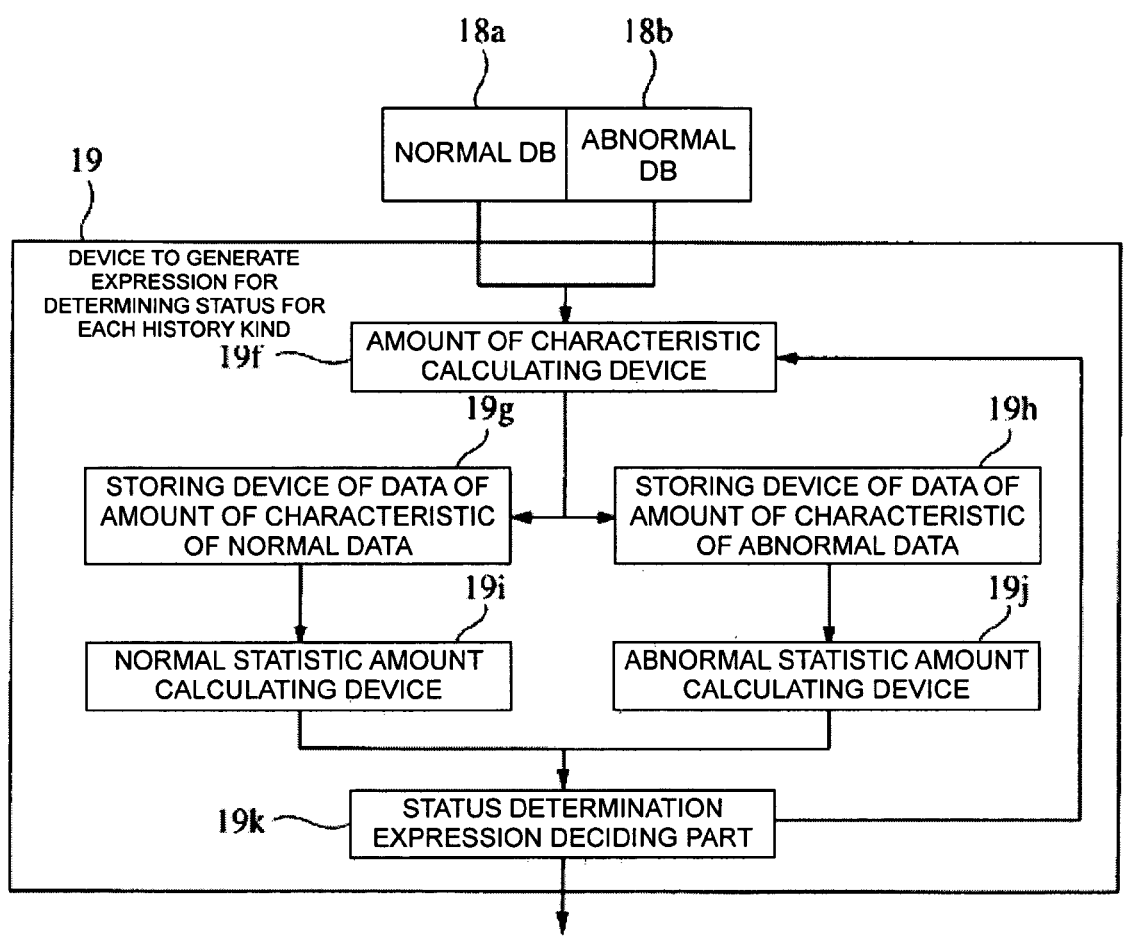
FIG. 13 shows a block diagram showing an example of an inner structure of a device to generate a determination calculating expression for determining a status for each history kind.

FIG. 13 shows other structure of the status determination expression generating device 19. According to this example, a normal and abnormal comparison system is realized. In other words, the data of the amount of characteristic for each history kind that is stored in the normal database 18a and the abnormal database 18b of the database for each history kind 18 is given to an amount of characteristic calculating device 19f. This amount of characteristic calculating device 19f may select an arbitrary specific function, and by using the selected specific function, the amount of characteristic calculating device 19f may calculate the data of the amount of characteristic that is stored in the above-described database. Then, the amount of characteristic of the abnormal data is stored in a storing device of the data of amount of characteristic of 19g of the normal data, and the amount of characteristic of the abnormal data is stored in a storing device of the data of amount of characteristic 19h of the abnormal data.

The amounts of characteristic of respective data that are calculated and accumulated in this way are given to corresponding statistic amount calculating devices 19i and 19j respectively. The statistic amount calculating device 19i for calculating the statistic amount of the amount of characteristic of the normal data may calculate a statistic amount such as the maximum value, the average value, and the standard deviation value or the like of the amount of characteristic of the given plural pieces of normal data. In the same way, the abnormal statistic amount calculating device 19j for calculating the statistic amount of the amount of characteristic of the abnormal data may calculate a statistic amount such as the maximum value, the average value, and the standard deviation value or the like of the amount of characteristic of the given plural pieces of abnormal data. In this case, it may obtain the amount of characteristic for each abnormal kind.

Then, the statistic amounts that are obtained by respective statistic amount calculating devices 19$i$ and 19$j$ are given to a status determination expression deciding part 19$k$ at a next chapter. As comparing the maximum value of the normal statistic amount (the normal maximum value) that is obtained by the normal statistic amount calculating device 19$i$ and the minimum value of the abnormal statistic amount (the abnormal minimum value) that is obtained by the abnormal statistic amount calculating device 19$j$, the status determination expression deciding part 19$k$ may determine if the normal maximum value<the abnormal minimum value. Then, if the statistic amount is provided with the above conditional expression, the status determination expression deciding part 19$f$ may determine that the specific function that is selected by the amount of characteristic calculating device 19$f$ is correct and may define this specific function in the status determining device 21. Thereby, the status determination device 21 may calculate the Euclidean distance by obtaining a square root of a sum of squares of the given amount of characteristic. Then, the status determination device 21 may determine the status depending on whether or not that Euclidean distance is not less than a threshold.

In addition, if the statistic amount is not provided with the above conditional expression, the selected specific function is defined as improper, so that the status determination expression deciding part 19$f$ requires changing of the specific function to be used from the amount of characteristic calculating device 19$f$. Receiving this, the amount of characteristic calculating device 19$f$ may select the specific function that is different from one that is set at a previous time and may calculate the amount of characteristic once again. Thereby, the specific function is changed, so that the amount of characteristic that is digitalized on the basis of the changed specific function is changed, and the statistic value is also changed. By repeatedly carrying out this processing, the status determination expression deciding part 19$k$ generates the statistic amount that is provided with the condition.

In the meantime, the condition in the status determination expression deciding part 19$k$ is not limited to the above-described condition, and various changes may be available. For example, the maximum value is made into a normal average+3 sigma and the minimum value is made into an abnormal average 3 sigma.

Figure 14:
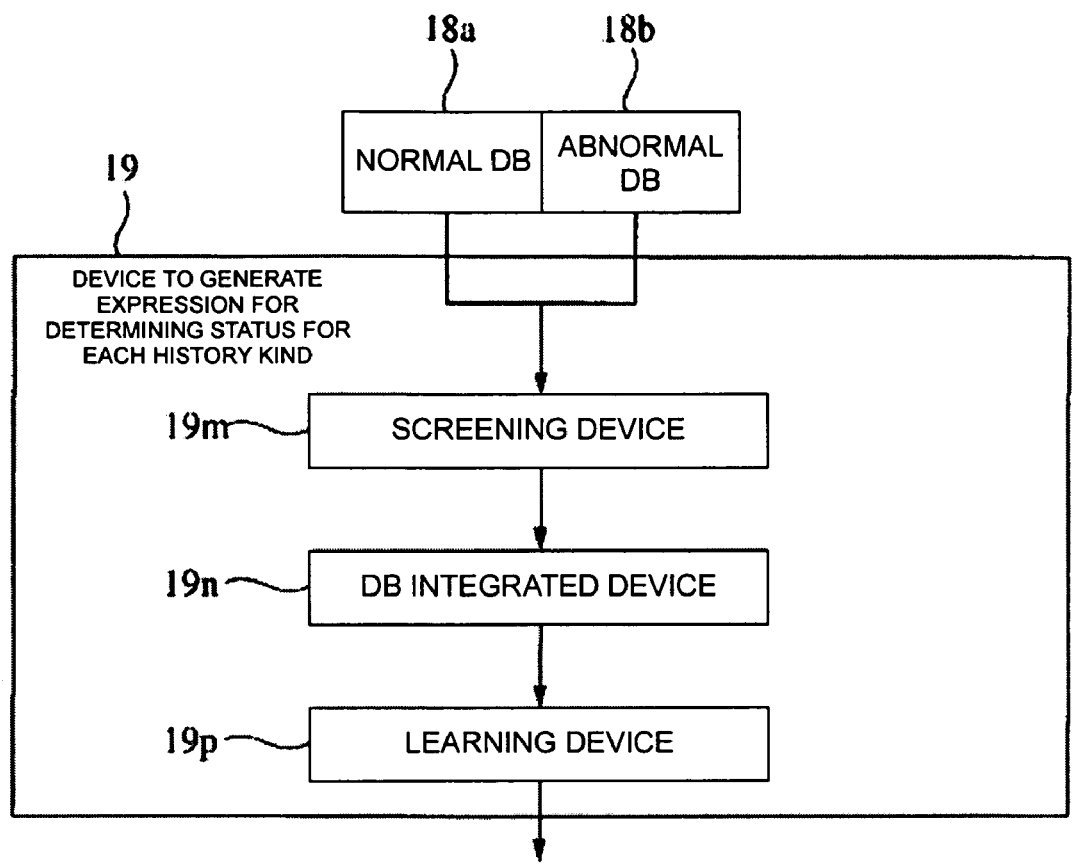
FIG. 14 shows a block diagram showing an example of an inner structure of a device to generate a determination calculating expression for determining a status for each history kind.

FIG. 14 shows further other structure of the status determination expression generating device 19. According to this example, a neural network system is realized. In other words, the data of the amount of characteristic for each history kind that is stored in the normal data bases 18$a$ and the abnormal database 18$b$ of the database for each history kind 18 is given to a screening device 19$m$. This screening device 19$m$ calculates an outlier of each database and deletes the data thereof. For example, the outlier may include (1) a value that is departed from an average±3σ, and (2) a value that is departed from an average±3σ obtained by calculating an average and a standard deviation without using six data, namely, first to third data from the maximum value and first to third data from the minimum value.

Giving the data that is screened by the screening device 19$m$ to a data integrated device 19$n$ to integrate the data. Then, a learning device 19$p$ learns (constructs a model of clustering) a neural network model in which the data of the amount of characteristic that is stored in the integrated database is made into input and the history level is made into output. As the learning processing, various methods to be used in the neural network can be used. Then, if the learning is completed, defining the neural network model of a learning result as a status determining device, this neural network model is set in the status determination device 21.

Figure 15:
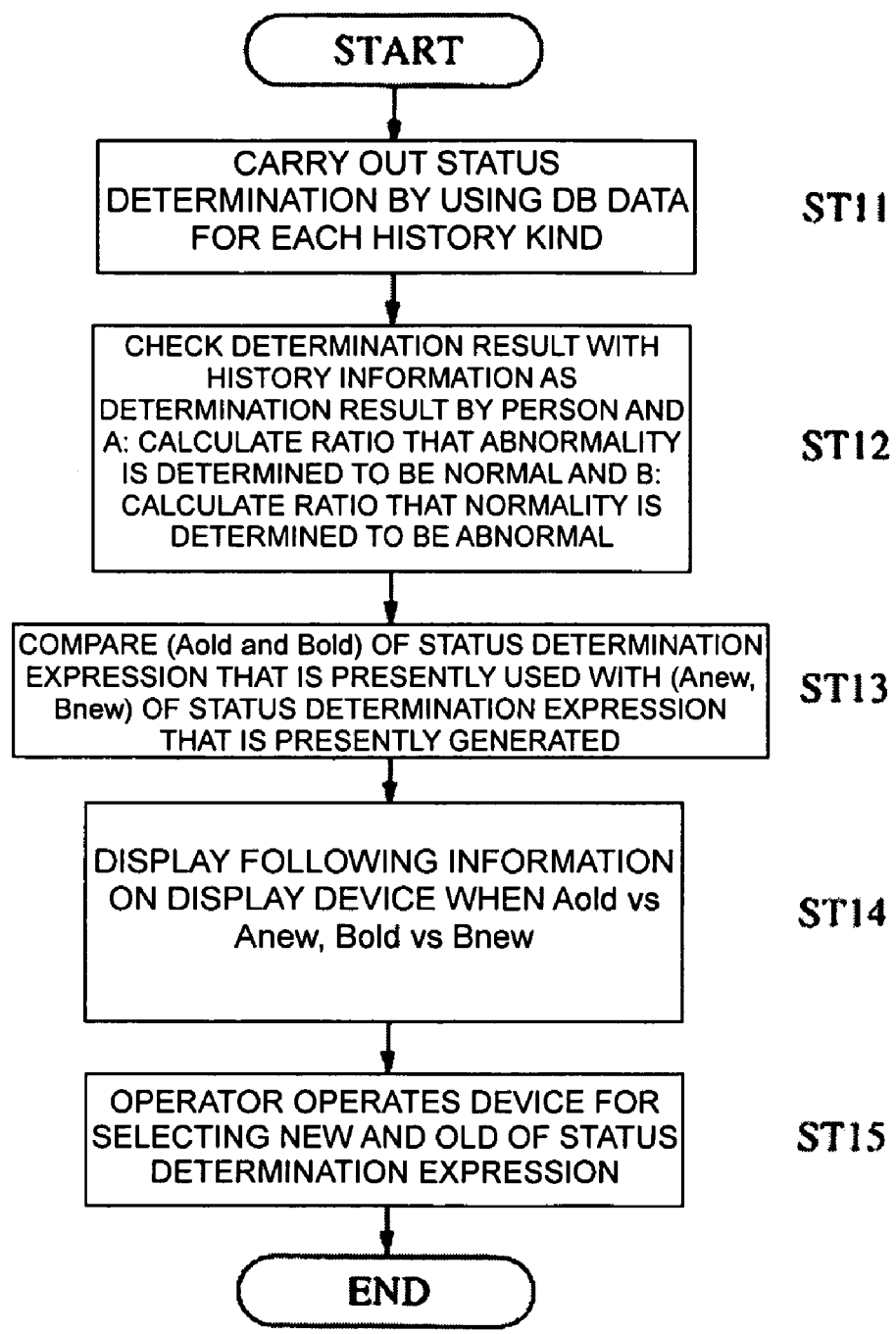
FIG. 15 shows a flow chart showing a function of a device to determine update of an update status determination expression.

The device to determine update of a status determination expression 22 has a status determination expression storing device determination expression database (illustration thereof herein omitted) to store and hold a determination expression that is generated by the device to generate an expression for determining a status for each history kind 19, and the device to determine update of a status determination expression 22 has a function to realize the flowchart shown in FIG. 15.

In other words, the device to determine update of a status determination expression 22 obtains the present status determination expression for each history kind from the status determination device 21, obtains a threshold that is generated from the device to set a threshold for each history kind 20, and carries out the status determination by using the data that is stored in the database for each history kind 18 (ST 11).

Consequently, the device to determine update of a status determination expression 22 may check the determination result that is obtained by executing the step 11 with the history information (the determination result by the person) that is stored in the database for each history kind 18 so as to obtain ratios of erroneous determination, respectively (ST 12). In this case, "A" is defined as a ratio to determine abnormality as normality and the obtained value is Anew. In addition, "B" is defined as a ratio to determine normality as abnormality and the obtained value is Bnew. Then, the values obtained in this way (namely, Anew, Bnew) are stored in the status determination expression storing device determination expression database. This determination expression database stores the values of A and B each time therein and the determination expression database is stored and held. Therefore, the device to determine update of a status determination expression 22 may read Aold and Bold that are the erroneous determination ratios of the status determination expression that is presently used from this determination expression database, and may compare them with Anew and Bnew that are the erroneous determination ratios that are obtained in the step and currently generated (ST 13).

Then, when Anew is less than Aold, the old and new erroneous determination ratios with respect to A and B are displayed on the display device (ST 14) and the operator is encouraged to update. In other words, while it is feared that the defective product is shipped if abnormality is determined to be normality, there is a demand that the ratio of the erroneous determination ratio with respect to A is decreased because a product that can be originally shipped is discarded when normality is erroneously determined to be abnormality. Therefore, according to the present invention, the device to determine update of a status determination expression 22 judges that the status determination expression should be updated when the erroneous determination ratio with respect to A is decreased as the step 14 and displays this.

Then, a final decision if the status determination ratio is updated or not will be done waiting for the instruction from the operator (ST 15). In other words, the operator may decide if the status determination ratio is updated or not in accordance with the old and new erroneous determination ratios with respect to A and B and other conditions, and by operating an input device, the operator may carry the decision. Therefore, the device to determine update of a status determination expression may carry out any one of the update processing of the status determination expression or continuation thereof in accordance with the decided content.

In the meantime, according to this example, the final judgment of update is performed by the operator, however, this final judgment may be automatically performed. In addition, in the case of only performing the determination of normality as the initial stage, since there may be the information only for B, in the step 14, Bold vs Bnew may be displayed when Bold>Bnew is established.

Figure 16:
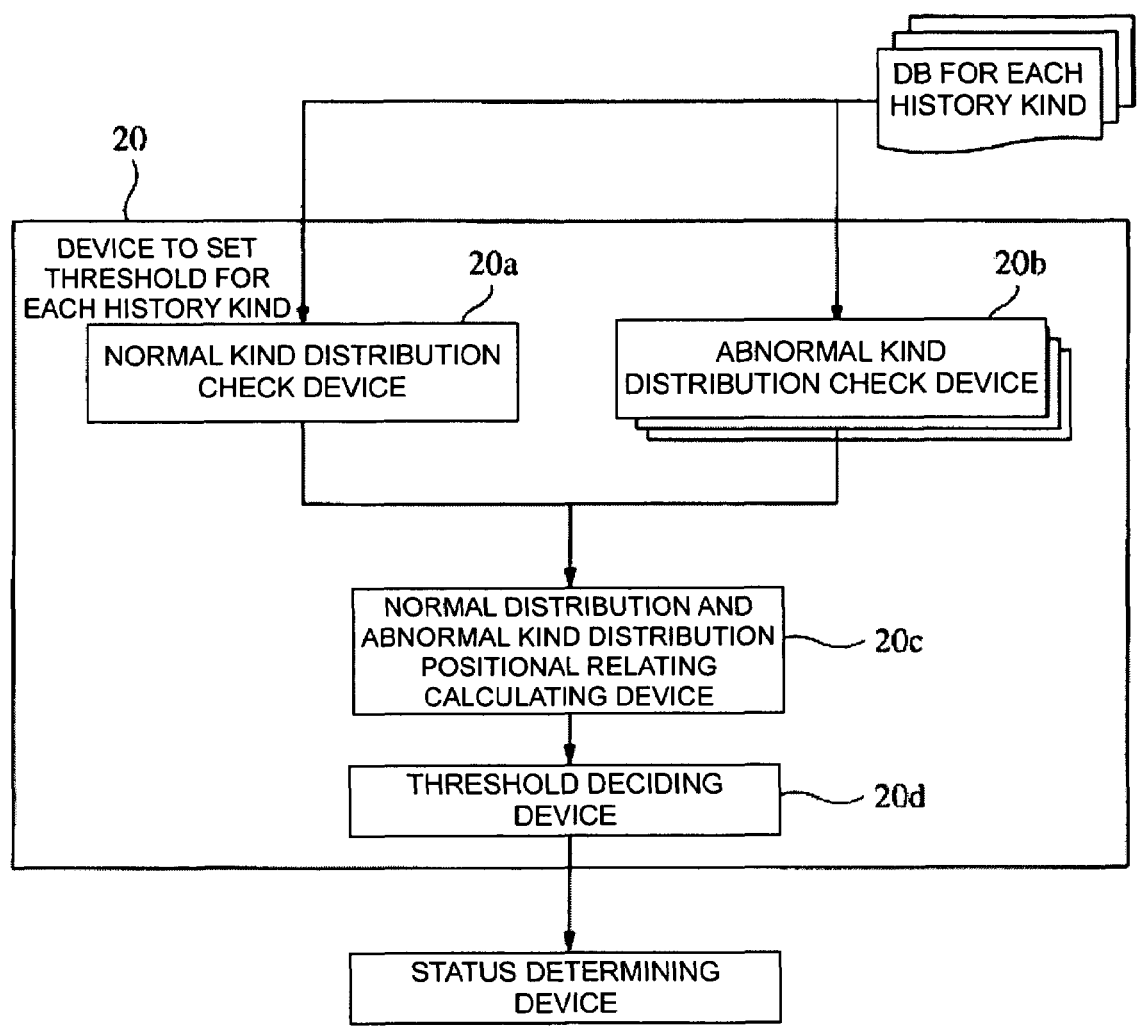
FIG. 16 shows a block diagram showing an example of an inner structure of a device to set a threshold for each history kind.

The device to set a threshold for each history kind 20 may set a threshed by the manual operation. In other words, as shown in FIG. 16, the device to set a threshold for each history kind 20 may give the amount of characteristic with respect to the normal data that is stored in the database for each history kind 18 to a normal kind distribution check device 20a, and the device to set a threshold for each history kind 20 may give the amount of characteristic with respect to the abnormal data that is stored in the database for each history kind 18 to an abnormal kind distribution check device 20b. When the abnormal kind is set, the amount of characteristic with respect to the abnormal data is given for each abnormal kind. In this case, the normal data and the abnormal data may be carved out on the basis of the history information, or they may be carved out on the basis of the determination result by the person.

Respective distribution check devices 20a and 20b may obtain the distribution status of the amount of characteristic for each obtained history kind, and for example, the distribution check devices 20a and 20b may calculate the average value, the medium value, the standard deviation, a quartile point, and $n \times \sigma$ ($n=1, 2, , ,$ ). Therefore, the calculated respective values are given to a normal distribution and abnormal kind distribution positional relating calculating device 20c. This normal distribution and abnormal kind distribution positional relating calculating device 20c may obtain a positional relation TX between the normal distribution and one abnormal kind distribution. For example, the normal distribution and abnormal kind distribution positional relating calculating device 20c may obtain the positional relations between the distributions of the all abnormal kinds and the al normal distributions, for example, a positional relation TA between the normal distribution and the abnormal kind A, a positional relation TB between the normal distribution and the abnormal kind B , , , or the like.

Here, the positional relation TX (X=A, B, C , , , ) is a numeric value of the amount of characteristic, and this can be obtained, for example, by TX=normality (average+3σ) ·an abnormal kind X (average·3σ). In addition, the average can be changed into the medium value, 3σ can be changed into the quartile point or $n \times \sigma$ ($n=1, 2, , ,$ ).

The positional relation TX between the normal distribution and each abnormal kind distribution that is obtained by the normal distribution and abnormal kind distribution positional relating calculating device 20c is given to a threshold deciding device 20d. The threshold deciding device 20d may check a mark of TX and may obtain ΔX in accordance with a rule that is described below.

When TX is negative, the normal distribution and the abnormal kind distribution partially overlap, so that a middle position of TX is assumed as ΔX. Specifically, this is obtained by the following expression.

$$\Delta X = \tfrac{1}{2} [\text{normality (average+3σ)+an abnormal kind } A \text{ (average·3σ)}]$$

When TX is 0 and positive, the normal distribution and the abnormal kind distribution do not overlap, so that ΔTX is set at the distribution side of the abnormal kind X. Specifically, this is obtained by the following expression.

$$\Delta X = \text{an abnormal kind } X \text{ (average·3σ)}$$

Then, obtaining ΔX with respect to all abnormal kinds, respectively, its minimum value is made into a threshold Δ (Δ=min (ΔX)). Then, in the above expression, the average can be changed into the medium value, 3σ can be changed into the quartile point or $n \times \sigma$ ($n=1, 2, , ,$ ).

Figure 17:
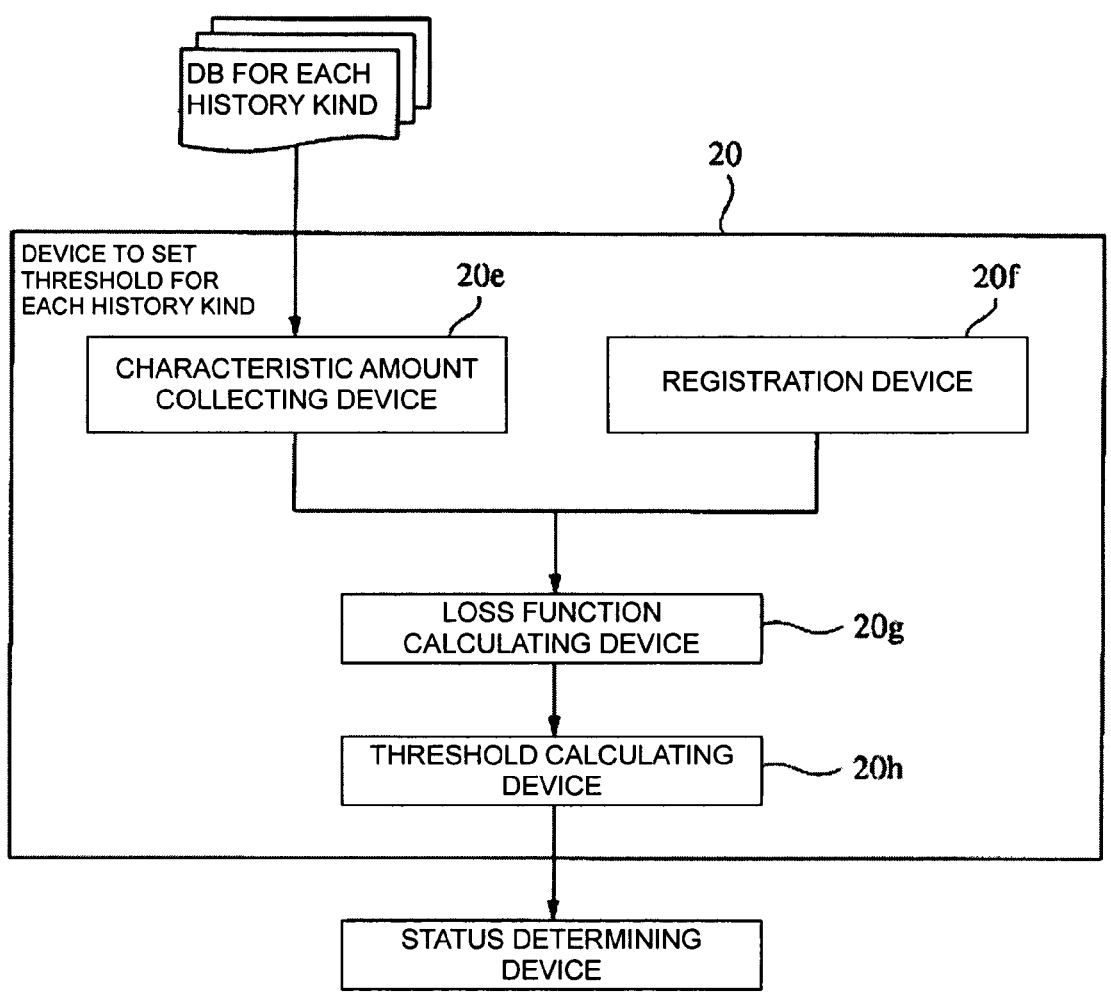
FIG. 17 shows a block diagram showing an example of an inner structure of a device to set a threshold for each history kind.

FIG. 17 shows other structure of the device to set a threshold for each history kind 20. According to the example shown in FIG. 16, the normal distribution and the abnormal distribution are needed, however, according to the present example, it is possible to set the device to set a threshold for each history kind 20 on the basis of one distribution.

Specifically, collecting the data stored in the database for each history kind 18, the values of all amounts of characteristic in the inspection object work 1 that is inspected by the inspection apparatus 10 are collected. Specifically, the standard deviation σ is obtained.

In addition, the device to set a threshold for each history kind 20 is provided with various registration devices. Specifically, the registration device registers (1) the discard cost A0 of the inspection object work, (2) the threshold Δ0 (an arbitrary level of the amount of characteristic), and (3) a rework cost A of the inspection object work. In this case, the discard cost is a cost that is expensed when the product is determined to be abnormal (defective) and is discarded. For example, there are costs for manufacturing and for discarding or the like. The rework cost is necessary to remake the inspection object work that is determined to be abnormal (defective) into a normal product by exchanging the parts thereof.

The amount of characteristic collected by a characteristic amount collecting device 20e and the registration information inputted in a registration device 20f are given to a loss function calculating device 20g at a next chapter. This loss function calculating device 20g calculates a loss function L on the basis of the following expression.

$$L = (A0/\Delta 0^2) \times \sigma^2$$

Then, giving the loss function L that is obtained in this way to a threshold calculating device 20h at a next chapter, a threshold Δ is calculated on the basis of the following expression.

$$\Delta = (A/A0)^{(1/2)} \times \Delta 0$$

In this case, an evaluation function L will be described below. Change of characteristic is change of a quality, and by indication this by a loss money amount, the quality is functioned as a management index. In other words, in a focused step, the cost to maintain the quality and sum of quality loss money amounts caused on and after the next step is managed by a threshold so as to balance them to be minimized.

In other words, when considering the quality by the cost expensed for stability of a function, the quality can be defined by economical loss and a management object (threshold) can be decided by the money amount. For example, when the product is delivered to a user after shipment, if its function is not stable, the user complains of the product and this leads to a loss. This is a loss of the user. On the other hand, inspecting the stability of the function, if the product is repaired or the product is discarded, this leads to an economical loss of the focused step. In addition, if the product is shipped so as not to cause a loss at the steps, at the user's side, the loss becomes serious. On the contrary, if the loss is completely solved at the steps, the loss at the step's side becomes large. It is important to these two losses are balanced to be minimized.

Figure 18:
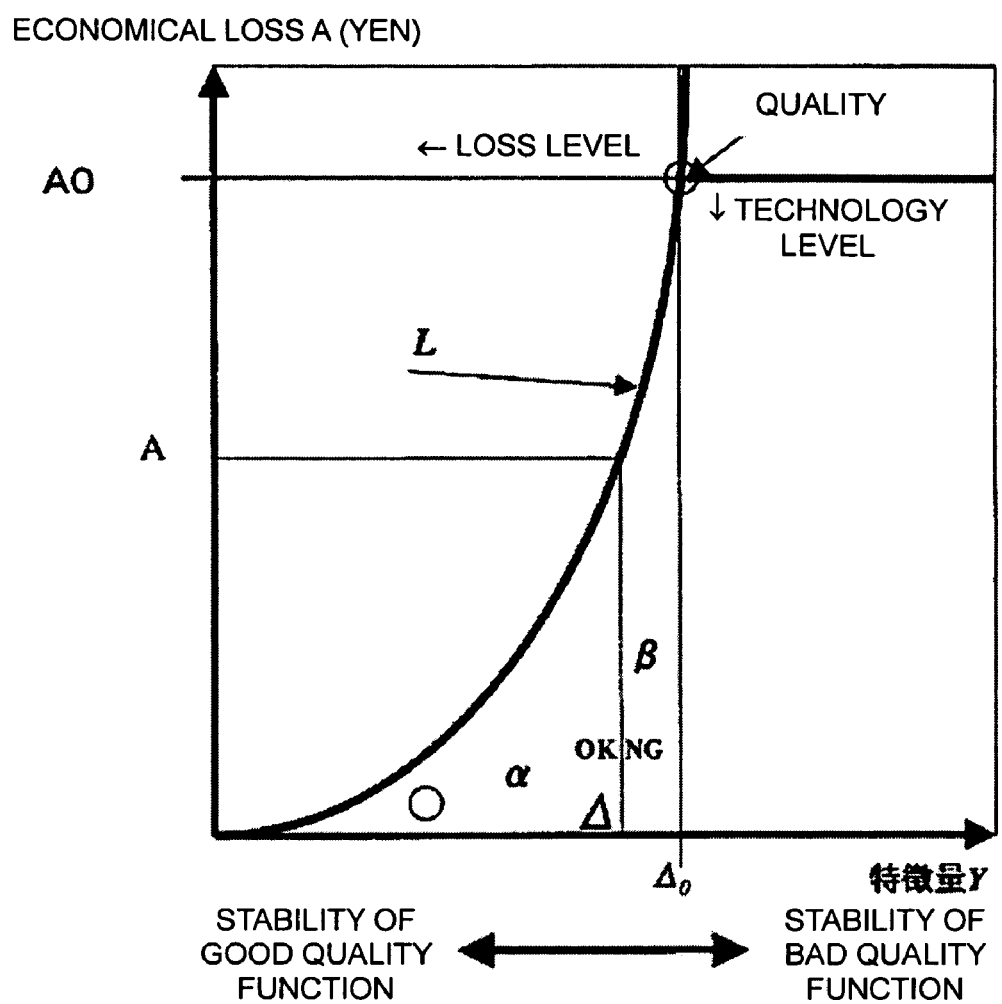
FIG. 18 shows an operation principle of the device to set a threshold for each history kind shown in FIG. 17.

The above-described two loss balances can be represented as shown in FIG. 18. In other words, the worse the quality of a certain characteristic amount Y is deteriorated, the higher the economical loss becomes. Then, NG is generally varied, so that if the quality (functionality) is deteriorated, the loss rapidly appears. Further, obtaining the threshold Δ by executing the above-described expression, an area of a region α at the OK side and an area of a region β at the NG side become equal and two losses are balanced so as to minimize the loss.

In addition, according to this method, it is possible to set the threshold only in one history kind, for example, only the normal data or only the abnormal data. Accordingly, during a period of time when only the normal determination is carried out, it is preferable to decide the threshold according to such a method.

Figure 19:
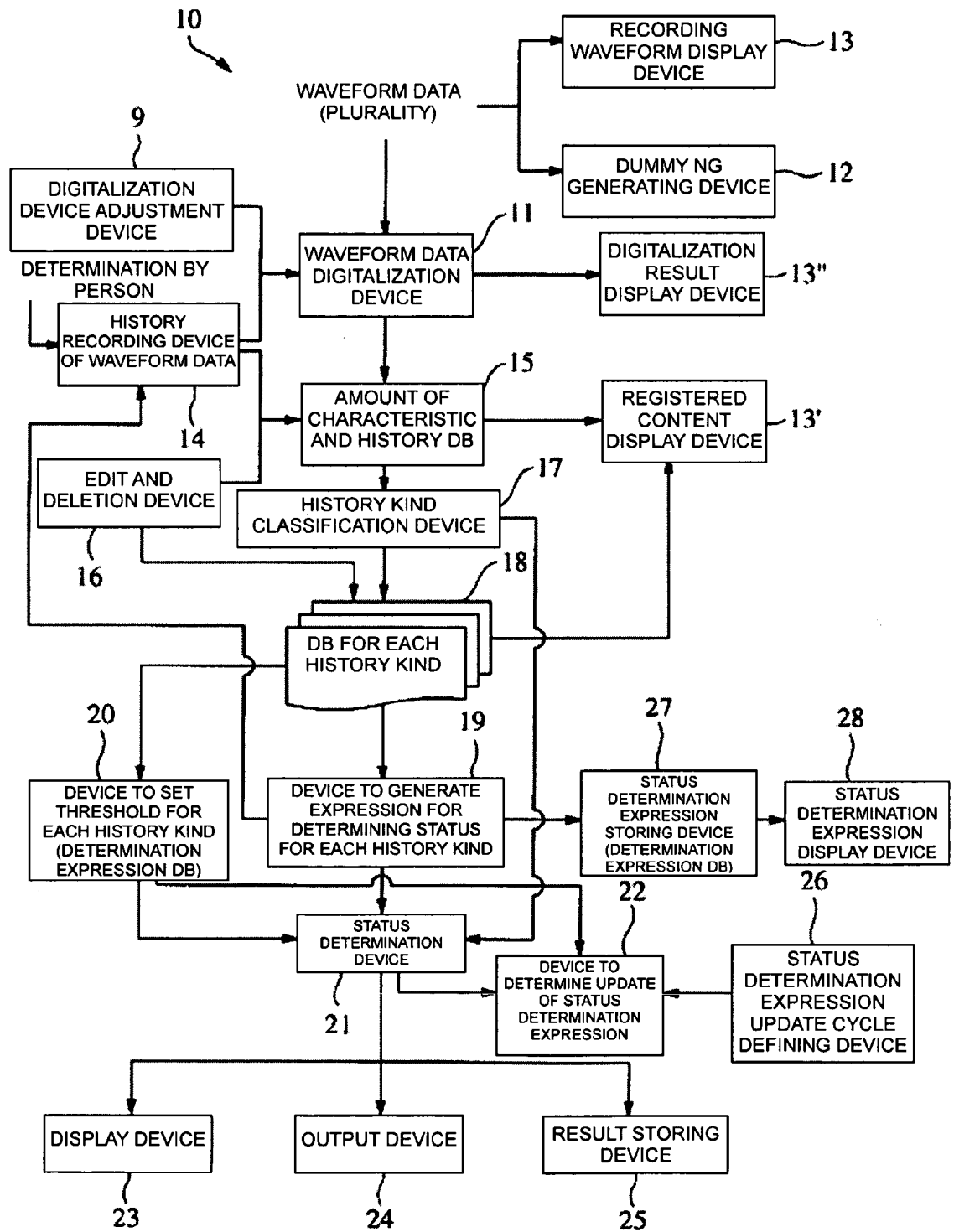
FIG. 19 shows a block diagram showing a first embodiment of an inspection apparatus (when an inspection is operated) according to the present invention.

FIG. 19 shows the inner structure of the present inspection apparatus 10 when the inspection is activated. According to the present embodiment, even when the inspection is activated, the algorithm is also made as explained with reference to FIG. 6 in parallel in order to correct the determination algorithm for good or bad determination. Therefore, a functional block for making the algorithm is also necessary, so that approximately the same structure is adopted as being obvious as compared to FIG. 6. Then, the activation of the inspection will be described below. In FIG. 19, the waveform data digitalizing device 11 obtains the waveform data of the inspection object work 1, digitalizes this waveform data, obtains the amount of characteristic thereof, and stores this amount of characteristic in the amount of characteristic and history data base 15. In addition, if the judgment with respect to the same object is carried out by a person, the determination result by the person is also stored in the amount of characteristic and history data base 15 as the history information.

Then, the data of the amount of characteristic that is stored in the amount of characteristic and history data base 15 is given to the status determination device 21 and the status determination (the good or bad determination) is carried out there. The obtained status determination result is displayed on the display device 23, or it is displayed on the output device 24, or it is stored in the result storing device 25.

On the other hand, learning upon activation of the inspection (creation and correction of the algorithm) is the same as that explained as above. In the meantime, since other structure and the operational effect are the same as the above-described embodiment, the same reference numerals are given to them and the detailed explanation is herein omitted.

Figure 20:
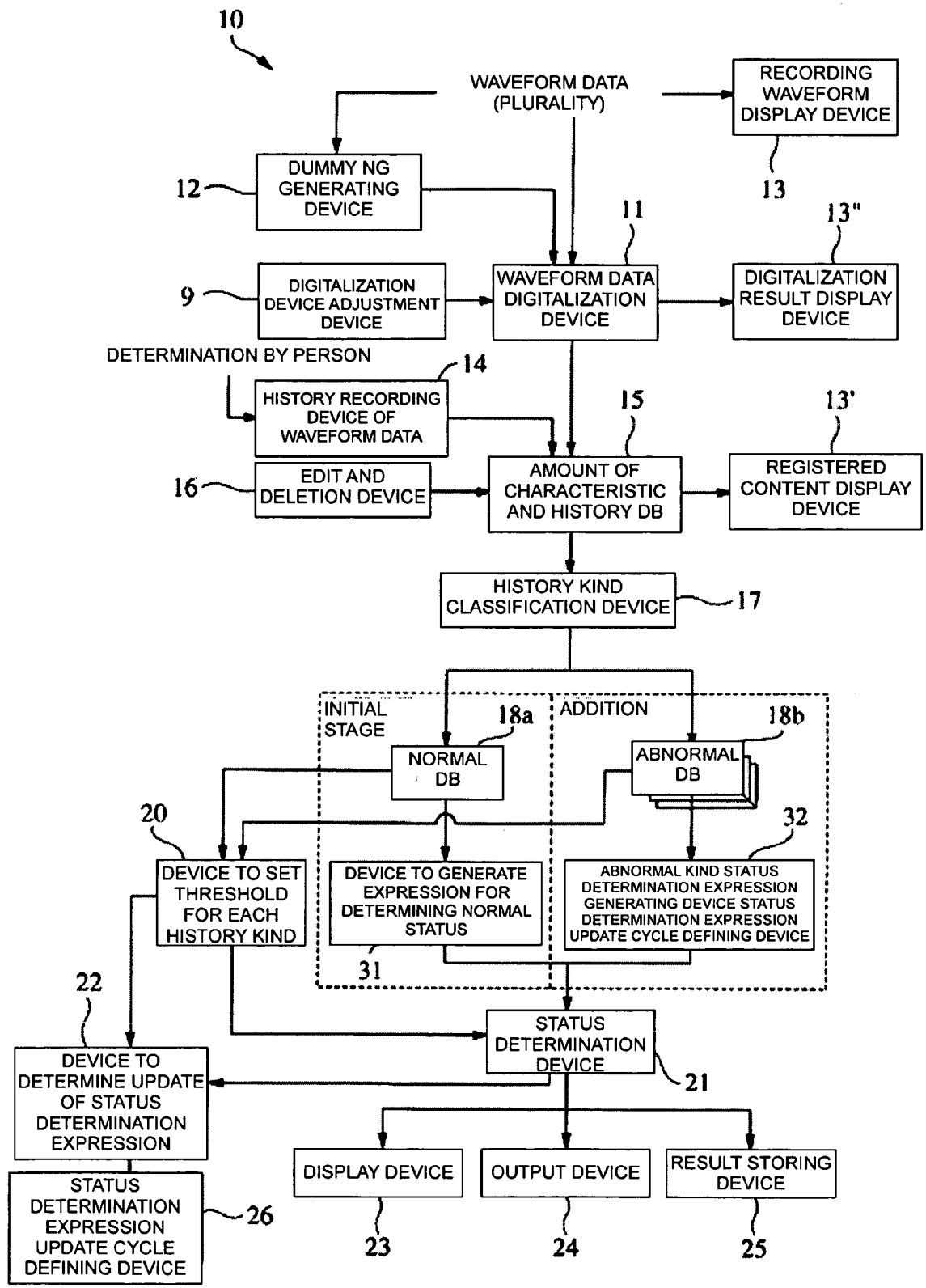
FIG. 20 shows a block diagram showing a second embodiment of an inspection apparatus (when making an algorithm) according to the present invention.

FIG. 20 shows a manner when the algorithm is created according to a second embodiment of the present invention. As shown in FIG. 20, the basic structure is the same as that of the above-described first embodiment, and the same reference numerals are given to the corresponding members (the processing parts) and a difference between the first and second embodiments will be mainly described below.

Obtaining the waveform data, the waveform data digitalizing device 11 digitalizes it, obtains each amount of characteristic, and stores the obtained amount of characteristic in the amount of characteristic and history data base 15. It is a matter of course that this amount of characteristic in the amount of characteristic and history database also stored the determination result by a person as the history information therein via the history recording device 14 of the waveform data. Then, the history kind classification device 17 may access the amount of characteristic and history database 15 on the basis of the history information; may extract the product having the normal history information and store it in the normal data base 18a; and may extract the product having the abnormal history information and store it in the abnormal data base 18b for each abnormal kind.

The amount of characteristic of the normal data that is stored in the normal data base 18a is given to a normal status determination expression generating device 31, and the status determination status expression for the normal status is calculated there to be transferred to the status determination device 21. On the other hand, the data of the amount of characteristic of the abnormal kind that is stored in the abnormal database 18b is given to an abnormal kind status determination expression generating device 32, and a status determination expression for the abnormal status is calculated there to be transferred to the status determination device 21.

In the meantime, as described above, according to the present invention, only the normal determination is carried out in the test of mass production or in the initial status of mass production or the like, and after that, the status determination combining the normal determination with the abnormal kind determination is carried out, and further, when the status shifts to the stable period of mass production, only the abnormal determination is carried out as a principle. Therefore, in accordance with this switching of the determination, at first, at the initial stage, the normal data base 18a and the normal kind status determination expression generating device 32 are provided without the abnormal database 18b and the abnormal kind status determination expression generating device 32. Then, when the defective determination is needed, the abnormal database 18b and the abnormal kind status determination expression generating device 32 may be added. It is a matter of course that the abnormal database 18b and the abnormal kind status determination expression generating device 32 can be provided from the very beginning.

Figure 21:
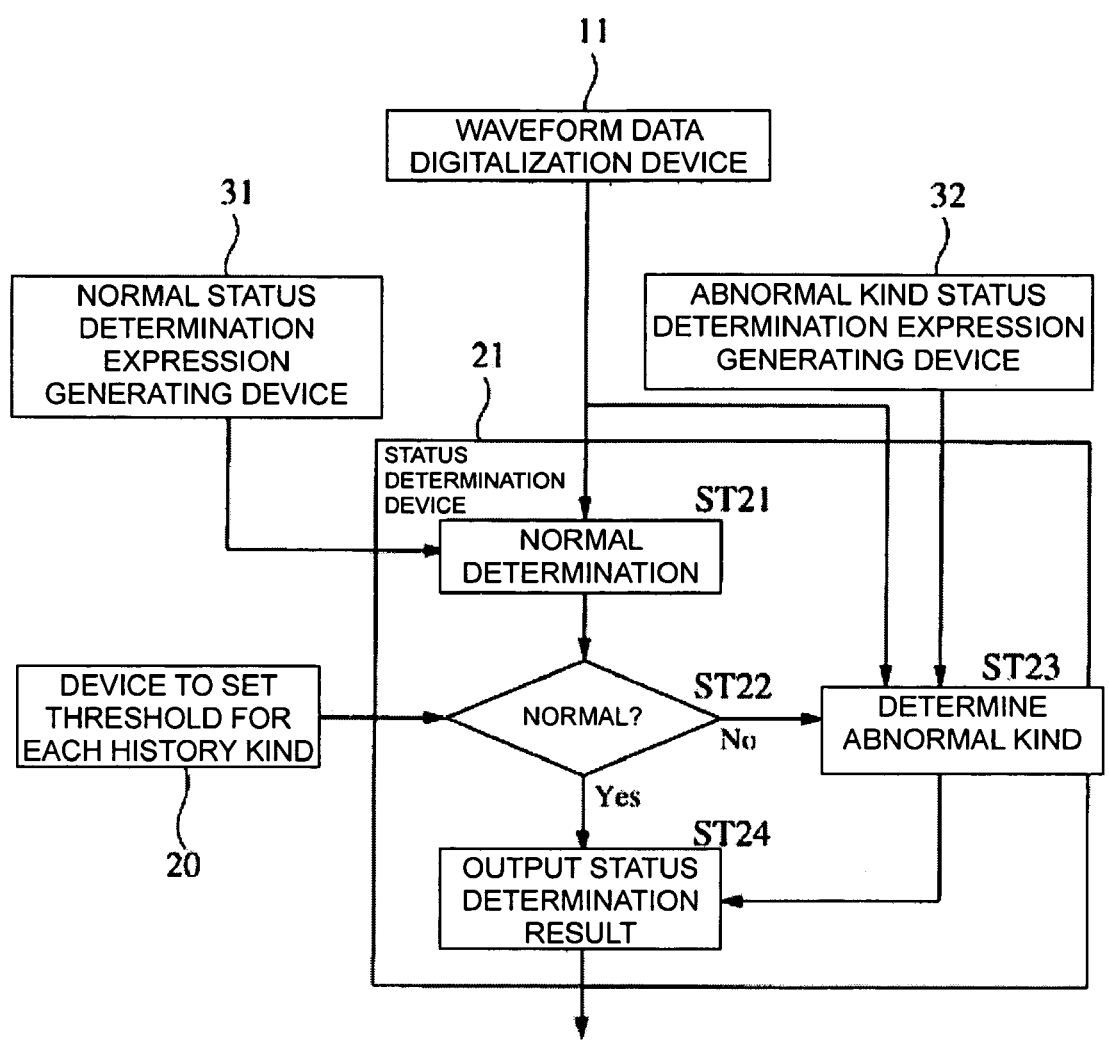
FIG. 21 shows a function of a status determination device.

Then, the status determination device 21 may carry out good or bad determination on the basis of the information that is provided from the normal status determination expression generating device 31 and the abnormal kind status determination expression generating device 32. The status determination device 21 can be configured by mounting a function to perform the processing, for example, the processing as shown in FIG. 21. In other words, at first, the status determination device 21 may carry out the normal determination (ST 21). In this normal determination, the status determination device 21 determines whether or not the inspection object work is normal (good) on the basis of the determination expression to be given from the normal status determination expression generating device 31 and the amount of characteristic of the waveform data of the inspection object that is obtained by the waveform data digitalization device 11.

Then, the status determination device 21 may judge if the judge result is normal or abnormal (ST 22), and if it is normal, the status determination device 21 outputs "normal (good)" as the status determination result (ST 24). In addition, if the judge result is not normal, the status determination device 21 may carry out determination for each abnormal kind (ST 23). In other words, the status determination device 21 specifies the abnormal kind of the inspection object work from the determination expression to be given from the abnormal kind status determination expression generating device 32 and the amount of characteristic of the waveform data of the inspection object that is obtained by the waveform data digitalization device 11. Then, the status determination device 21 may output the specification result as the status determination result (ST 24).

Figure 22:
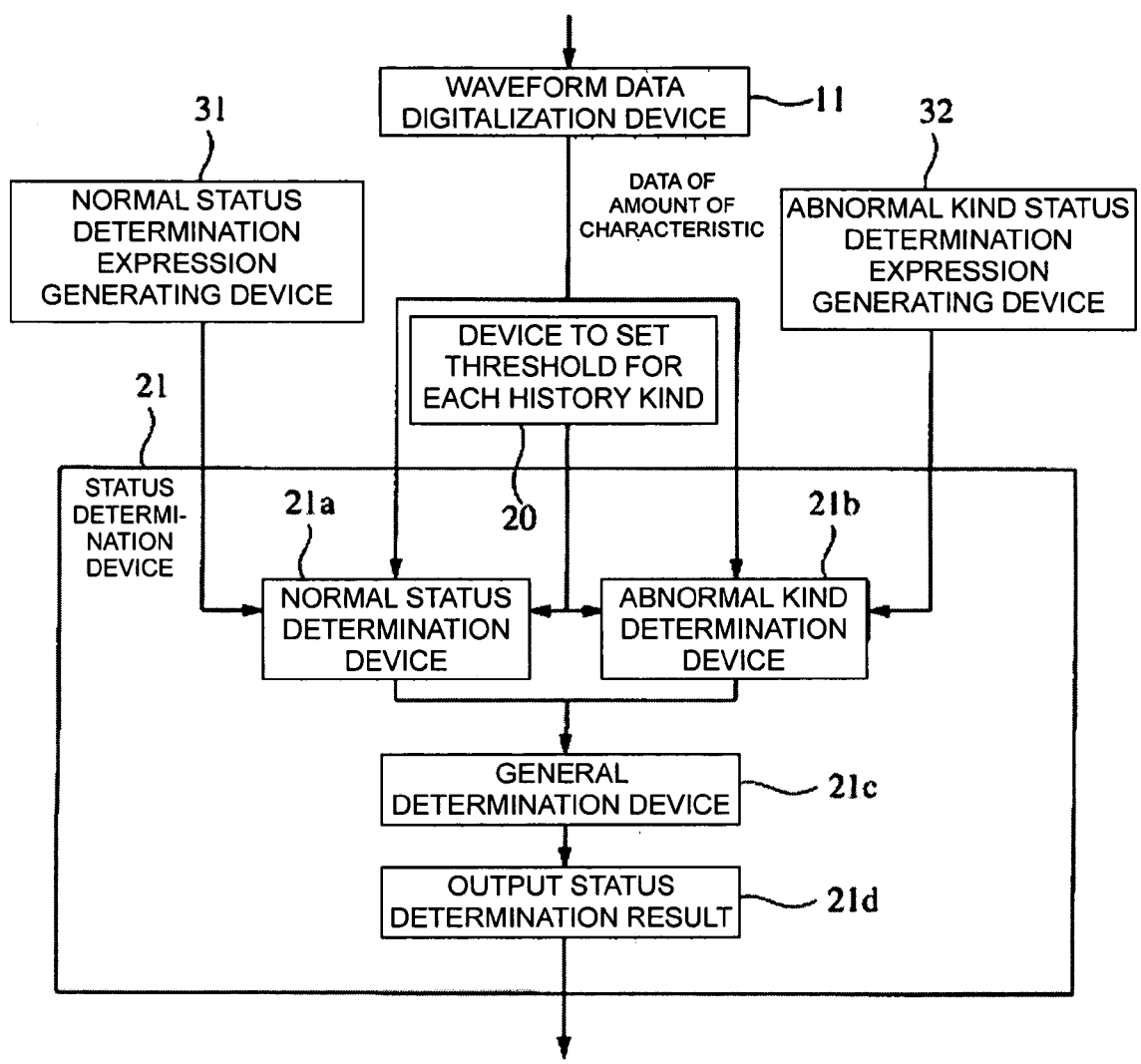
FIG. 22 shows other structure of the status determination device.

According to this example, at first, the status determination device 21 may carry out the normal determination and may determine the status that is not normal to be the abnormal kind. However, the present invention is not limited to this, and for example, as shown in FIG. 22, giving the amount of characteristic of the waveform data that is obtained from one inspection object work to usage determination devices 21a and 21b, the usage determination devices 21a and 21b may carry out the parallel processing to obtain "the status is normal or not" and "the status corresponds to a prescribed abnormal kind or not".

Then, providing each of the obtained determination results to a general determination device 21c and generally judging respective determination results in the general determination device 21c, the general determination device 21c may decide the status determination finally. The algorithm of the general judgment to be done at this time can be executed, for example, in accordance with the following rules.

Figure 23:
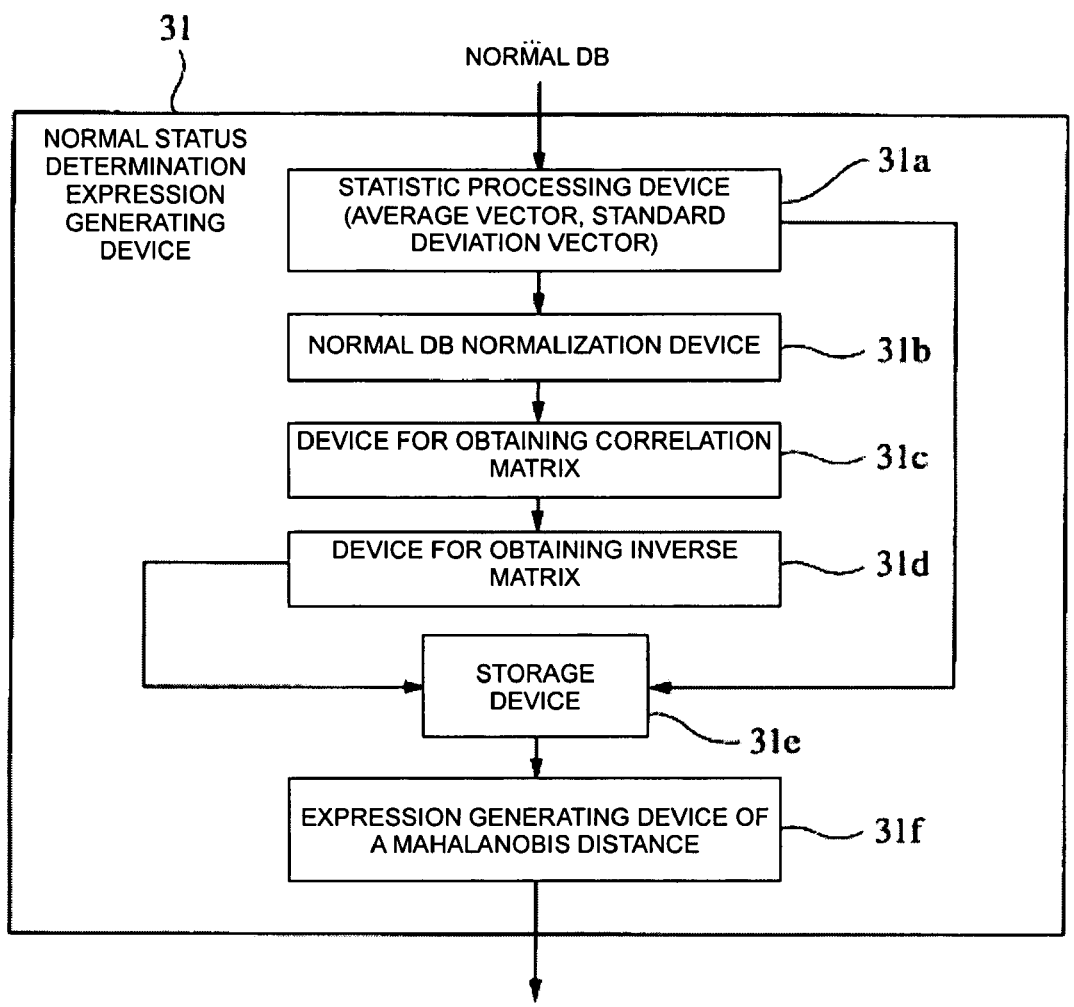
FIG. 23 shows a block diagram showing an example of an inner structure of a device to generate a normal status determination expression.

Normal determination YES and abnormal kind determination
YES→Output abnormal kind determination
Normal determination YES and abnormal kind determination
NO→Output normal determination
Normal determination NO and abnormal kind determination
YES→Output abnormal kind determination
Normal determination NO and abnormal kind determination
NO→Output abnormal kind determination The normal status determination expression generating device 31 and the abnormal kind status determination expression generating device 32 have the same structures as the device to generate an expression for determining a status for each history kind 19 in the first embodiment, however, according to the present embodiment, the normal status determination expression generating device 31 is configured as shown in FIG. 23 and the determination expression that is different from the abnormal kind status determination expression generating device 32 is used.

In other words, providing the amount of characteristic of the normal data that is stored in the normal data base 18a to a statistic processing device 31a, the statistic amounts of all amount of characteristic are calculated in the statistic processing device 31a. The statistic amount is defined as the average and the standard deviation. In other words, obtaining the average value and the standard deviation for each amount of characteristic, an average vector making the average values of respective amount of characteristic into one unit and a standard deviation vector making the standard deviations of respective amounts of characteristic into one unit are obtained.

Then, the obtained statistic amount is provided to a normal database normalization device 31b, and the normal database normalization device 31b normalizes the data that is stored in the normal database 18a by the average vector and the standard deviation vector. The numeric values of each amount of characteristic are varied, so that regulation and normalization of the statistic amount are carried out. Further, obtaining a correlation matrix of each amount of characteristic by a device 31c for obtaining a correlation matrix and transferring the obtained correlation matrix to a device 31d for obtaining an inverse matrix, the inverse matrix of the correlation matrix is also obtained.

Then, the average vector, the standard deviation vector, and the inverse matrix that are obtained by the above-described devices are stored in a storing device 31e. Giving each data that is stored in this storing device to an expression generating device 31f of a Mahalanobis distance, a Mahalanobis distance is obtained.

In other words, upon obtaining a Mahalanobis distance $D^2$, measuring the data of n pieces of inspection object works assuming that the number of characteristic amounts is k and the values of respective items are X1, X2 , , , Xk, averages m1, m2 , , , and mk for each amount of characteristic and standard deviations σ1, σ2 , , , σk are obtained. Assuming that a component of the inverse matrix of the correlation matrix in this time as aij, the Mahalanobis distance is defined by the following expression. The expression generating device 31f generates this expression and sets it in the status determination device 21.

$$D^2 = 1/k \sum_{ij} aij \times (Xi - mi)/\sigma i \times (Xj - mj)/\sigma j \qquad \text{[Expression 1]}$$

Where, all of n pieces of data are necessarily in the same history kind.

Figure 24:
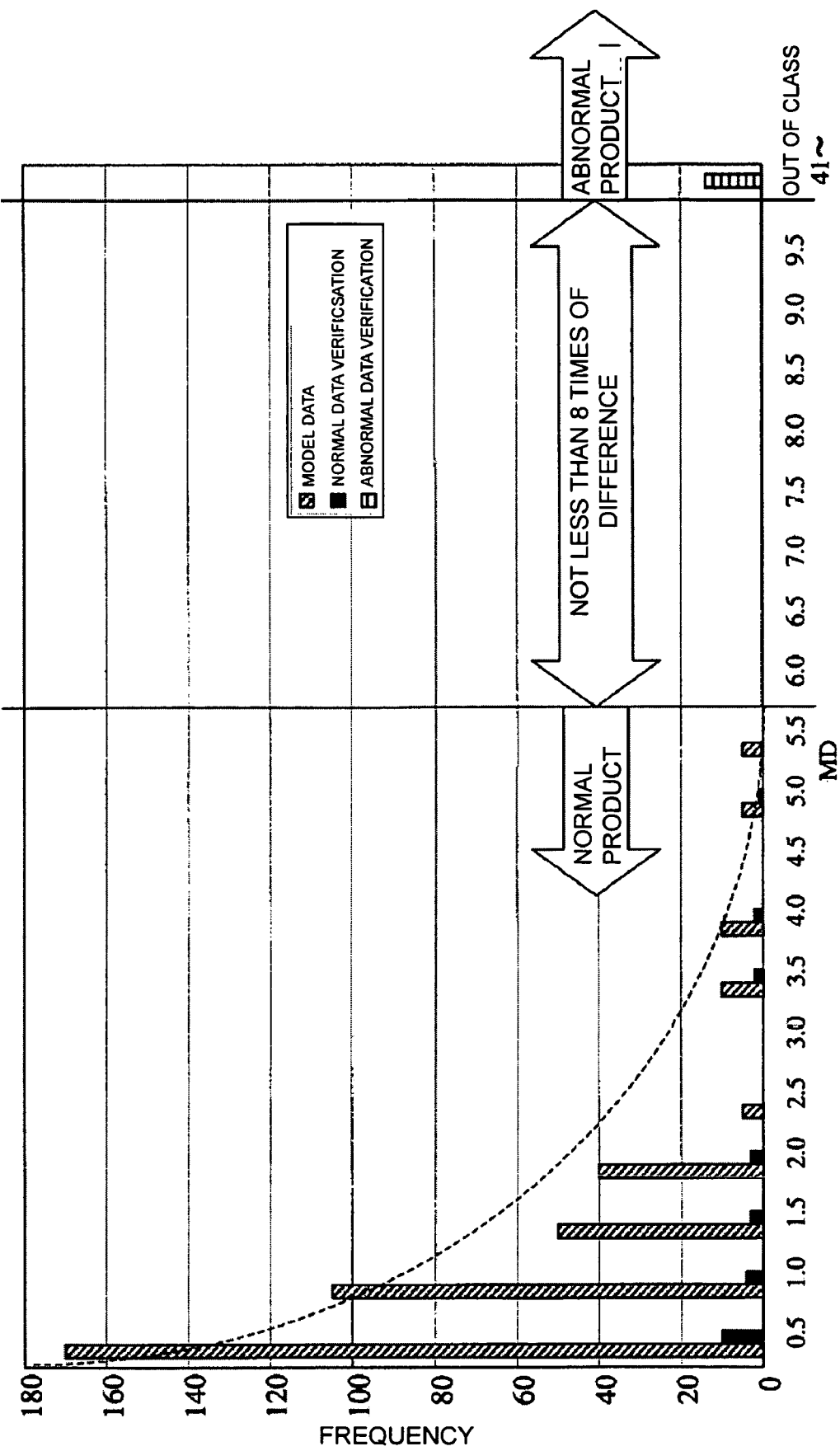
FIG. 24 shows a function (1).

A pattern of the mass production normal data is similar to ideal normal data, so that the mass production normal data is plotted in the vicinity of an evaluation reference and the Mahalanobis distance takes a value around 1. On the contrary, the abnormal data is plotted far from the evaluation reference in accordance with a difference between the pattern of the abnormal data and the pattern of the normal data, and the Mahalanobis distance takes a large value (refer to FIG. 24). Therefore, it is possible to determine normal or abnormal simply depending on whether or not the Mahalanobis distance is close to 1. In the meantime, evaluating a reliability contribution ratio of the Mahalanobis distance of a specific function to be used, a function to delete a low contribution ration may be added.

In other words, according to the conventional inspection apparatus, carving out the data for a time necessary for calculation from the waveform data of all times that are sampled, and further, making one unit of data obtained by dividing the carved out data with a prescribed number of data into one frame, the amount of characteristic of plural kinds (for example, 40 kinds) is extracted in one frame. Then, with respect to each amount of characteristic obtained from all frames, for each amount of characteristic of the same kind, a calculated value of a typical amount of characteristic is obtained according to an average method and other various methods. Therefore, 40 pieces of the calculated values of a typical characteristic amount are calculated in accordance with the kind of the amount of characteristic. Then, the good or bad determination may be determined by using all of the 40 pieces of the calculated values of a typical characteristic amount or a prescribed number of the calculated values of a typical characteristic amount selected from among the 40 pieces thereof. Leaving aside the number of the calculated values of a typical characteristic amount to be used, the calculated values of a typical characteristic amount are compared by amount of characteristic (calculated value of a typical characteristic amount) to be determined.

Figure 25:
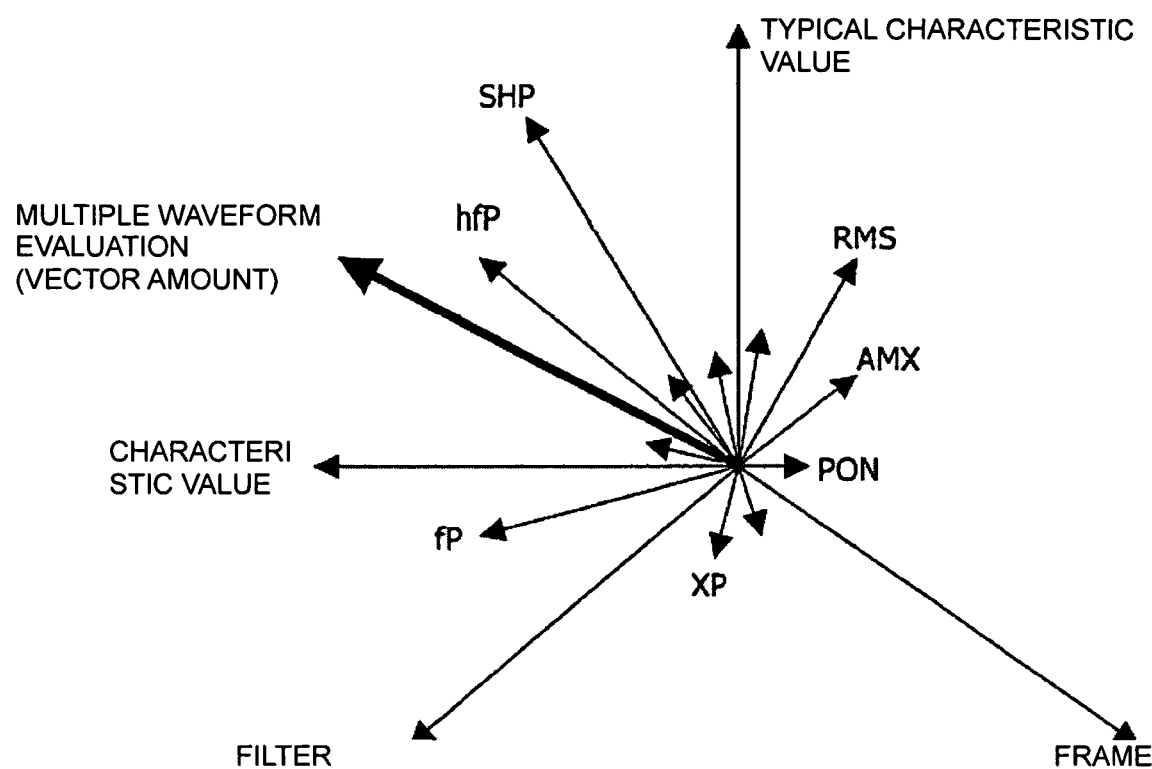
FIG. 25 shows a function (1).

On the contrary, according to the present embodiment, the obtained plural kinds of amounts of characteristic are integrated to be converted into one numeric value (a multiple waveform evaluation: a vector amount). This waveform data numeric value and image of each amount of characteristic are as shown in FIG. 25. It is natural that a model upon carrying out good or bad determination is also a vector amount that is generated by obtaining plural amounts of characteristic. Accordingly, the good or bad determination is carried out by comparing this model with the vector amount on the basis of the waveform data of the inspection object, namely, by comparing two vector amounts with each other, and if a distance between both vector amounts is in a prescribed range, the inspection object is determined to comply with the model, and if the both vector amounts are separated, the inspection object is determined to be different from the model. In other words, in the case of only the normal determination, a model of a reference may have at least one numeric value (a multiple waveform evaluation: a vector amount) that is obtained by integrating the amounts of characteristic of plural kinds, and by obtaining a distance between the inspection object and the numeric value, the good or bad determination is carried out. In other words, after calculating the vector amount integrating respective amounts of characteristic (respective calculation values of a typical characteristic amount obtained on the basis of plural frames in fact), it is possible to carry out the good or bad determination by performing the calculation processing to obtain the distance only at once. Then, the distance between the both vector amounts may be calculated by the Mahalanobis distance according to the present embodiment, and further, the distance between the both vector amounts may be calculated by various methods including the Euclidean distance and others.

Figure 26:
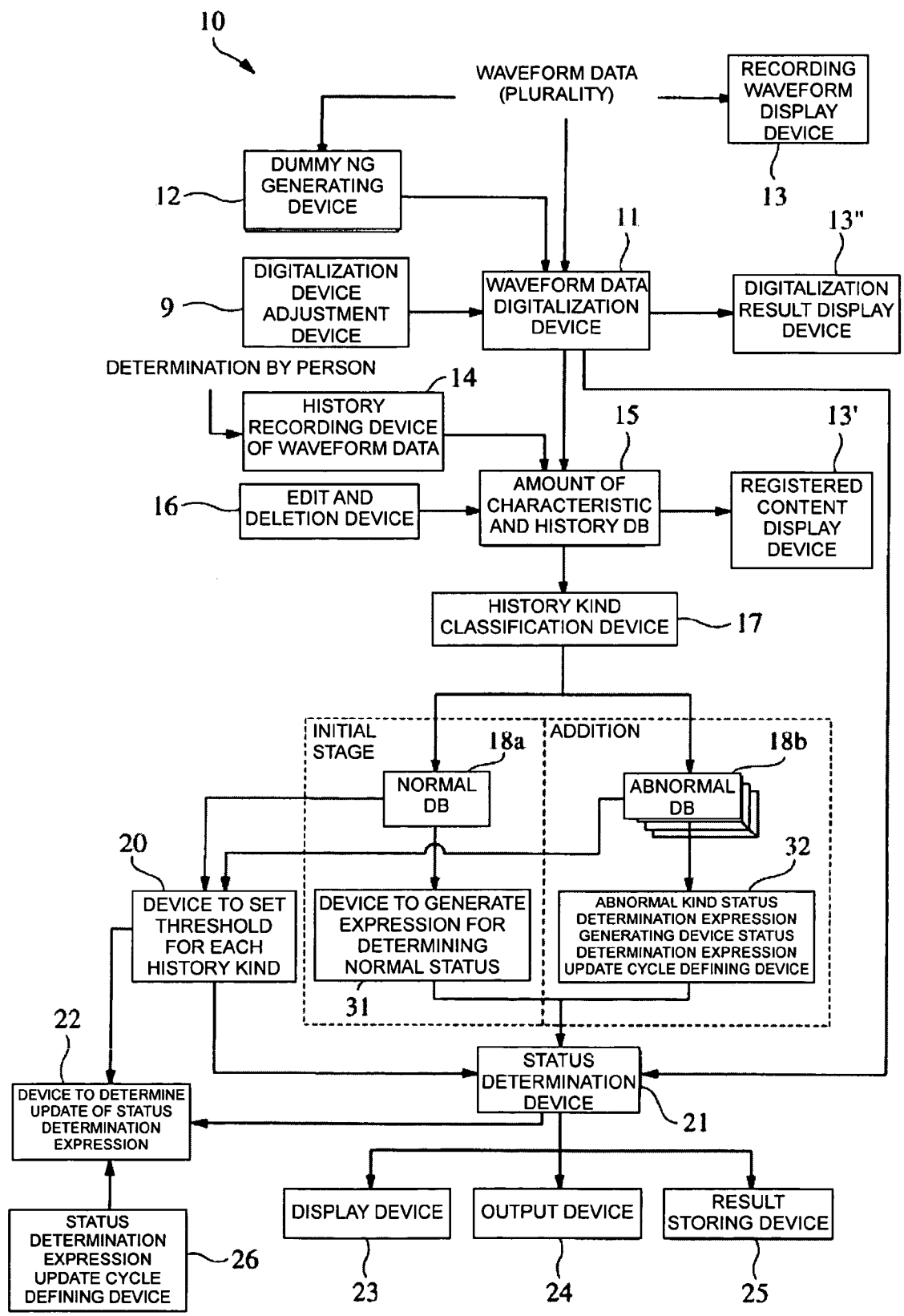
FIG. 26 shows a block diagram showing a second embodiment of an inspection apparatus (when the inspection is operated) according to the present invention.

FIG. 26 shows the inner structure of the present inspection apparatus 10 upon activating the inspection. According to the present embodiment, even when the inspection is activated, the algorithm is also made as explained with reference to FIG. 20 in parallel in order to correct the determination algorithm for good or bad determination. Therefore, a functional block for making the algorithm is also necessary, so that approximately the same structure is adopted as being obvious as compared to FIG. 20. Then, the activation of the inspection will be described below. In FIG. 20, the waveform data of the inspection object work 1 is given to the waveform data digitalizing device 11 to be digitalized there, and then, the amount of characteristic is obtained to be stored in the amount of characteristic and history data base 15. In addition, when the judgment by a person is carried out with respect to the same object at the same time, the history information (the determination result by the person) is also stored in the amount of characteristic and history database 15.

Then, the data of the amount of characteristic that is stored in the amount of characteristic and history data base 15 is given to the status determination device 21 and the status determination (the good or bad determination) is carried out there. The obtained status determination result is displayed on the display device 23, or it is displayed on the output device 24, or it is stored in the result storing device 25.

On the other hand, learning upon activation of the inspection (creation and correction of the algorithm) is the same as that explained as above. In the meantime, since other structure and the operational effect are the same as the above-described embodiment, the same reference numerals are given to them and the detailed explanation is herein omitted.

The inspection apparatus 10 of the above-described embodiments can be applied to an inspection field of an abnormal noise, an assembly error, and an output property. In addition, the inspection apparatus 10 of the above-described embodiments can be applied to an in line for mass production and to an off line for performing the inspection or the like of a test product other than the mass production. Then, more specifically, for example, the inspection apparatus 10 according to the present embodiment can be applied as an inspection machine of a driving module of an automobile such as an engine (a sound) of the automobile and a transmission (vibration) or the like, an inspection machine of a motor actuator module of an automobile, and an inspection machine of a motor actuator module of an automobile such as an electric door mirror, an electric power sheet, and an electric column (positioning of a steering wheel) or the like. Further, the inspection apparatus 10 according to the present embodiment can be applied as an evaluation apparatus of an abnormal noise, an assembly error, and an output property during development of the above-described modules, and further, as an evaluation apparatus of a test machine during development.

In addition, the inspection apparatus 10 of the above-described embodiments can be applied as an inspection machine of a motor driving electric household appliance such as a refrigerator, indoor and outdoor equipments of an air conditioner, a washing machine, a cleaner, and a printer or the like and as an evaluation apparatus of an abnormal noise, an assembly error, and an output property during development of the above-described motor driving electric household appliances.

Furthermore, the inspection apparatus 10 of the above-described embodiments can be applied as a facility diagnosis unit for performing status determination (abnormal status/normal status) of a facility such as a NC finishing machine, a semiconductor plant, and a food plant or the like. Conventionally, it is a predetermined fact and a fixed idea that a determination expression (a determination rule) of normal or abnormal is made on the basis of the sample data when abnormal, however, according to this idea, it is determined to be normal or abnormal only from the sample data when normal. Just after introduction, a facility unit is generally used while adjusting it (or while adjusting and changing setting of an operational parameter), so that "the abnormal status" is generated unsteadily and the abnormal status can be prevented from being generated by performing maintenance or adjusting the equipment well.

In the meantime, some of the abnormal status are provided with a solution at an activation stable period of the facility equipment so that they are not generated. This means that a phenomenon that some of "abnormal status" of the status determination of the facility equipment are not generated is similar to a phenomenon that some of "defective products" of the inspection object are not generated, and this means that the present invention can be applied as the facility diagnosis unit for performing the status determination (the abnormal status/the normal status). Upon applying the present invention to this facility diagnosis unit, the status before the facility is stably activated may correspond to "an initial status". In addition, with respect to the abnormal kind knowledge, a portion requiring maintenance adjustment periodically due to a secular change of the facility equipment itself is found among the facility equipments after the activation of the facility equipment becomes stable, so that the abnormal status (two status, namely, abnormality and an abnormal kind) of that portion is specified, and the abnormal determination knowledge may be generated on the basis of the data for each abnormal kind. If a solution I the abnormal determination knowledge is provided and the abnormal status is not generated, deleting the abnormal kind knowledge of this abnormal kind, the determination processing may be carried out with the abnormal kind knowledge of this abnormal kind deleted.

In addition, the facility is not limited to the plant, and the facility may include a vehicle such as an automobile and an airplane or the like, and the facility can be also applied as a diagnosis equipment for determining the status of various products. For example, taking the vehicle as an example, a normal knowledge only on the basis of the data of the normal status with respect to the engine status is generated at the test of mass production. It is natural that the abnormal status is generated at the test of mass production, however, some of the abnormal status are not generated by improvement of the test model. Therefore, at an initial stage of the test of mass production, making a determination rule only from the normal data, at a stage that a mass production is close to completion by improving the test model and solving some of the abnormal status to prevent generation thereof, some abnormal kinds are specified. Then, from the data of that abnormal kind, the abnormal kind knowledge is generated. Thus, it is possible to determine the normal status from the specific abnormal status. In this way, accumulating the data and the knowledge from the stage of test of mass production, and making a diagnosis equipment to determine if the status is normal or abnormal and determine which of abnormal kinds the status is, this diagnosis equipment as a finished product is mounted on an automobile and an airplane that are allowed to be in a market so as to enable to diagnose normal or abnormal on the basis of the vibration of the engine.

What is claimed is:

1. An inspection method using an inspection apparatus for extracting amount of characteristic to an inputted waveform signal and determining a status of an inspection object on the basis of the extracted amount of characteristic, the method comprising the steps of:
   determining whether or not the status complies with a normal status by using a normal knowledge that is generated on the basis of only data of the normal status at an initial stage; and
   determining the status by using the normal knowledge and an abnormal kind knowledge, the abnormal kind knowledge being generated on the basis of data of the abnormal status that are collected in accordance with repeat of the normal status determination,
   wherein, as a result of determination of the status by using the normal knowledge and the abnormal kind knowledge, if the abnormal kind is not detected on the basis of the abnormal kind knowledge, deleting the abnormal kind knowledge of the abnormal kind, the determination processing is carried out with the abnormal kind knowledge of the abnormal kind deleted.

2. An inspection apparatus for extracting amount of characteristic to an inputted waveform signal and determining a status of an inspection object on the basis of the extracted amount of characteristic, having:
   a first mode for determining whether or not the status complies with a normal status by using a normal knowledge that is generated on the basis of only data of the normal status of the inspection object; and
   a second mode for determining whether or not the status is normal and whether or not the status complies with a prescribed abnormal kind by using the normal knowledge that is generated on the basis of the data of the normal status of the inspection object and an abnormal kind knowledge that is generated on the basis of data of the prescribed abnormal kind;
   wherein, at the initial stage when the abnormal kind is not specified, the inspection apparatus determines the status in the first mode; and the inspection apparatus determines the status in the second mode at a prescribed timing after the initial stage.

3. The inspection apparatus according to claim 2, comprising:
   a dummy abnormal data generating device for generating the dummy abnormal data by processing the data of the normal status;
   wherein the inspection apparatus carries out the normal status determination processing by using the dummy abnormal data that is generated by the dummy abnormal data generating device so as to enable the evaluation of the normal knowledge.

4. The inspection apparatus according to claim 2,
   wherein a threshold to determine whether or not the status is the normal status in the normal knowledge is set at a value that a cost caused by discarding the inspection object that is determined not to be normal and a cost expensed to modify the inspection object that is determined not to be normal into normal are balanced.

5. The inspection apparatus according to claim 4,
   wherein the threshold to determine whether or not the status is the normal status in the normal knowledge is set by a registration device having information of a quality function limit, discard cost information, and adjustment cost information registered therein;
   a loss function calculating device for calculating a loss function on the basis of the information of the registration device; and
   a threshold calculating device for calculating a threshold on the basis of the loss function of the loss function calculating device.

6. An inspection apparatus for extracting amount of characteristic to an inputted waveform signal and determining a status of an inspection object on the basis of the extracted amount of characteristic, comprising:
   a normal status determining device for determining whether or not the status complies with a normal status by using a normal knowledge that is generated on the basis of only data of the normal status; and
   an abnormal kind determining device for determining whether or not the status complies with a prescribed abnormal kind by using an abnormal kind knowledge that is generated on the basis of data of the prescribed abnormal kind;
   wherein, at the initial stage when the abnormal kind is not specified, the inspection apparatus determines the status only by the normal status determining device; and the inspection apparatus determines overall the status by operating the normal status determining device and the abnormal kind determining device at a prescribed timing after the initial stage.

7. The inspection apparatus according to claim 6, wherein the abnormal kind determining device is additionally incorporated into the apparatus later after the initial stage.

8. The inspection apparatus according to claim 6,
wherein, the normal status determining device calculates a vector making plural amounts of characteristic into one unit to decide the status on the basis of a distance between the vectors.

9. The inspection apparatus according to claim 6,
wherein at least one of the normal status determining device and the abnormal kind determining device calculates a vector making plural amounts of characteristic into one unit to decide the status on the basis of a distance between the vectors.

10. A facility diagnosis unit for extracting amount of characteristic to an inputted waveform signal and determining a status of a facility on the basis of the extracted amount of characteristic, comprising:

a normal status determining device for determining whether or not the status complies with a normal status by using a normal knowledge that is generated on the basis of only data of the normal status of the facility that is a diagnosis object; and an abnormal kind determining device for determining whether or not the status complies with a prescribed abnormal kind by using an abnormal kind knowledge that is generated on the basis of data of the prescribed abnormal kind;

wherein, at the initial stage when the abnormal kind is not specified, the facility diagnosis unit determines the status only by the normal status determining device; and the facility diagnosis unit determines overall the status of the facility by operating the normal status determining device and the abnormal kind determining device at a prescribed timing after the initial stage.

* * * * *